United States Patent [19]

Itoh et al.

[11] 4,245,099
[45] Jan. 13, 1981

[54] 2-ACYL-6-AMINOMETHYLPHENOL DERIVATIVES

[75] Inventors: Hiroyuki Itoh, Osaka; Mitoshi Konno, Kyoto; Takao Tokuhiro, Nagaokakyo; Sadahiko Iguchi, Yahata; Masaki Hayashi, Takatsuki, all of Japan

[73] Assignee: Ono Pharmaceutical Co., Ltd., Osaka, Japan

[21] Appl. No.: 60,113

[22] Filed: Jul. 24, 1979

[30] Foreign Application Priority Data

Jul. 27, 1978 [JP] Japan .................................. 53-91031

[51] Int. Cl.³ .......................................... C07D 213/50
[52] U.S. Cl. ..................................... 546/315; 546/328; 549/70; 260/347.3; 260/347.7; 424/263; 424/320; 424/330; 424/325; 424/275; 424/285; 424/324; 564/179; 564/185; 564/212; 564/219
[58] Field of Search ............ 260/562 A, 562 B, 562 P, 260/347.3, 347.7, 570.9; 546/314, 315, 328; 549/70

[56] References Cited

U.S. PATENT DOCUMENTS

| | | | |
|---|---|---|---|
| 3,809,721 | 5/1974 | Schultz et al. | 260/562 B |
| 4,083,868 | 4/1978 | Zaugg et al. | 260/562 A |

OTHER PUBLICATIONS

March "Advanced Organic Chemistry" (McGraw-Hill) (1968).

*Primary Examiner*—Henry R. Jiles
*Assistant Examiner*—Robert T. Bond
*Attorney, Agent, or Firm*—Sughrue, Rothwell, Mion, Zinn and Macpeak

[57] ABSTRACT

A 2-acyl-6-aminomethylphenol derivative having the formula (I):

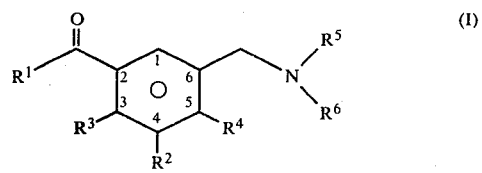

wherein $R^1$ represents a straight chain or branched chain alkyl group of 1 to 6 carbon atoms unsubstituted or substituted with 1 to 3 halogen atoms; a hydrogen atom or a group having the formula (II):

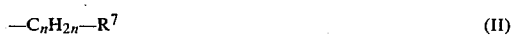

wherein n represents 0 or an integer of 1 to 6; $R^7$ represents a cycloalkyl group of 3 to 8 carbon atoms unsubstituted or substituted with at least one lower alkyl group; a phenyl group unsubstituted or substituted with at least one lower alkyl group, a halogen atom, a lower alkoxy group or a lower alkylthio group; a lower alkoxy group; a lower alkylthio group; a lower alkylsulfinyl group; a lower alkylsulfonyl group; an N-lower alkylamino group; an N,N-di-lower alkylamino group; or a pyridyl, furyl or thienyl group; $R^2$ represents a straight chain or branched chain alkyl group of 1 to 6 carbon atoms; a cycloalkyl group of 4 to 8 carbon atoms unsubstituted or substituted with at least one lower alkyl group; a phenyl group unsubstituted or substituted with at least one lower alkyl group, a lower alkoxy group, a lower alkylthio group or a halogen atom; or a lower alkylthio group; $R^3$ and $R^4$ each represents a hydrogen atom or $R^2$ and $R^3$ or $R^2$ and $R^4$ when taken together represent an alkylene group of 2 to 5 carbon atoms unsubstituted or substituted with 1 or 2 lower alkyl groups; $R^5$ represents a hydrogen atom or a lower alkyl group; and $R^6$ represents a hydrogen atom, a lower alkyl group or an acyl group, and the pharmaceutically acceptable acid addition salt thereof having antiinflammatory, analgesic, antipyretic, diuretic and hypotensive effects that can be used for preventing and curing diseases caused by inflammation, edema, hypertension, etc. are disclosed. Also disclosed is a process for preparing such derivative or a pharmaceutically acceptable acid addition salt thereof.

37 Claims, No Drawings

2-ACYL-6-AMINOMETHYLPHENOL DERIVATIVES

BACKGROUND OF THE INVENTION

1. Field of the Invention

This invention relates to a novel 2-acyl-6-aminomethylphenol derivative and a process for preparing the same. More particularly, this invention relates to a 2-acyl-6-aminomethylphenol derivative useful as a medicine, especially as an anti-inflammatory agent, of the formula (I):

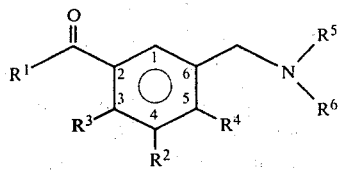

wherein $R^1$ represents a straight chain or branched chain alkyl group of 1 to 6 carbon atoms unsubstituted or substituted with 1 to 3 halogen atoms; a hydrogen atom or a group having the formula (II):

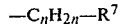

wherein n represents 0 or an integer of 1 to 6; $R^7$ represents a cycloalkyl group of 3 to 8 carbon atoms unsubstituted or substituted with at least one lower alkyl group; a phenyl group unsubstituted or substituted with at least one lower alkyl group, a halogen atom, a lower alkoxy group or a lower alkylthio group; a lower alkoxy group; a lower alkylthio group; a lower alkylsulfinyl group; a lower alkylsulfonyl group; an N-lower alkylamino group; an N,N-di-lower alkylamino group; or a pyridyl, furyl, thienyl group; $R^2$ represents a straight chain or branched chain alkyl group of 1 to 6 carbon atoms; a cycloalkyl group of 4 to 8 carbon atoms unsubstituted or substituted with at least one lower alkyl group; or a phenyl group unsubstituted or substituted with at least one lower alkyl group, a lower alkoxy group, a lower alkylthio group or a halogen atom; or a lower alkylthio group; $R^3$ and $R^4$ each represents a hydrogen atom or $R^2$ and $R^3$ or $R^2$ and $R^4$ when taken together represent an alkylene group of 2 to 5 carbon atoms unsubstituted or substituted with 1 or 2 lower alkyl groups; $R^5$ represents a hydrogen atom or a lower alkyl group; and $R^6$ represents a hydrogen atom, a lower alkyl group or an acyl group, and the pharmaceutically acceptable acid addition salt thereof.

2. Description of the Prior Art

Conventional non-steroid acidic anti-inflammatory agents have been considered disadvantageous in that they have a side effect of developing a complication of gastric ulcer. As a result of studies on a novel anti-inflammatory agent free from the defect of the conventional anti-inflammatory agents, the compound of this invention which will be described in more detail hereinafter has been found. The compound of this invention has anti-inflammatory, analgesic, antipyretic, diuretic and hypotensive effects, and can be used for preventing and curing diseases caused by inflammation, edema, hypertension, etc.

SUMMARY OF THE INVENTION

Accordingly, a principal object of the present invention is to provide a non-steroid anti-inflammatory agent which is substantially free from the side effects which accompany conventional anti-inflammatory agents.

Another object of the present invention is to provide a compound having anti-inflammatory, analgesic, antipyretic, diuretic and hypotensive effects that can be used for preventing and curing diseases caused by inflammation, edema, hypertension, etc.

Still a further object of the present invention is to provide a compound having the above effects but free from the side effect of gastric ulcers.

Another object of the present invention is to provide a method for synthesizing such a compound.

These and other objects of the present invention are accomplished by the 2-acyl-6-aminomethylphenol compound of the present invention.

DETAILED DESCRIPTION OF THE INVENTION

This invention relates to novel 2-acyl-6-aminomethylphenol derivatives and a process for preparing the same.

More particularly, this invention relates to 2-acyl-6-aminomethylphenol derivatives and pharmaceutically acceptable acid addition salts thereof represented by the formula (I):

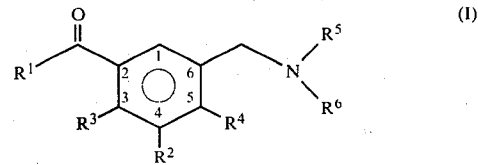

wherein $R^1$ represents a straight chain or branched chain alkyl group of 1 to 6 carbon atoms unsubstituted or substituted with 1 to 3 halogen atoms; a hydrogen atom or a group having the formula (II):

wherein n represents 0 or an integer of 1 to 6; $R^7$ represents a cycloalkyl group of 3 to 8 carbon atoms unsubstituted or substituted with at least one alkyl group; a phenyl group unsubstituted or substituted with at least one lower alkyl group, a halogen atom, a lower alkoxy group or a lower alkylthio group; a lower alkoxy group; a lower alkylthio group; a lower alkylsulfinyl group; a lower alkylsulfonyl group; an N-lower alkylamino group; an N,N-di-lower alkylamino group; or a pyridyl, furyl or thienyl group; $R^2$ represents a straight chain or branched chain alkyl group of 1 to 6 carbon atoms; a cycloalkyl group of 4 to 8 carbon atoms unsubstituted or substituted with at least one lower alkyl group; a phenyl group unsubstituted or substituted with at least one lower alkyl group, a lower alkoxy group, a lower alkylthio group or a halogen atom; or a lower alkylthio group; $R^3$ and $R^4$ each represents a hydrogen atom or $R^2$ and $R^3$ or $R^2$ and $R^4$ when taken together represent an alkylene group of 2 to 5 carbon atoms unsubstituted or substituted with 1 or 2 lower alkyl groups; $R^5$ represents a hydrogen atom or a lower alkyl group and $R^6$ represents a hydrogen atom, a lower alkyl group or an acyl group, which are useful as pharmaceuticals, especially as anti-inflammatory agents.

The term "lower al(kyl)" used herein for "lower alkyl group", "lower alkoxy group", "lower alkylthio group", "lower alkylsulfinyl group", "lower alkylsulfonyl group", "N-lower alkylamino group", "N,N-dilower alkylamino group" and "lower alkanol" means a straight chain or branched chain alkyl group, preferably a methyl or ethyl group.

The term "halogen atom" means a fluorine, chlorine, bromine or iodine atom.

The —$C_nH_{2n}$— in the group of the general formula (II) represents a straight chain or branched chain alkylene group of 1 to 6 carbon atoms or a single bond.

The alkyl group of 1 to 6 carbon atoms represented by $R^1$ and $R^2$ is methyl, ethyl, propyl, butyl, pentyl, hexyl or their isomers.

The compounds of the formula (I) wherein $R^2$ and $R^3$ when taken together or $R^2$ and $R^4$ when taken together represent an alkylene group of 2 to 5 carbon atoms unsubstituted or substituted with 1 or 2 lower alkyl groups are those of the formula:

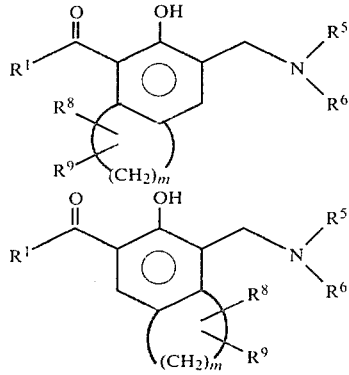

wherein m is an integer of 2 to 5, $R^8$ and $R^9$, which may be the same or different, represent a hydrogen atom, or a lower alkyl group and all the other variables are as defined above.

The acyl group represented by $R^6$ is a formyl group, an alkanoyl group of 2 to 5 carbon atoms optionally substituted with a halogen atom or a benzoyl group unsubstituted or substituted with at least one lower alkyl group, a hydroxyl group or a halogen atom.

Preferred $R^2$ group is a straight chain or branched chain alkyl group of 1 to 4 carbon atoms (more preferably, a tert-butyl group) or a phenyl group or when the compound of the formula (III) or (IV) is tetrahydronaphthol or indanol wherein m represents 3 or 4, $R^8$ represents a hydrogen atom or a methyl group and $R^9$ represents a hydrogen atom.

Preferred $R^5$ group is a hydrogen atom, methyl group or ethyl group.

Preferred $R^6$ group is a hydrogen atom, a methyl group, an ethyl group or a chloroacetyl group.

Preferred examples of the pharmaceutically acceptable acid addition salts are inorganic salts such as hydrochloride, hydrobromide, hydroiodide, sulfate, phosphate and nitrate and organic salts such as acetate, lactate, tartarate, citrate, methanesulfonate, ethanesulfonate, benzenesulfonate, toluenesulfonate and isethionate.

The conventional non-steroidal anti-inflammatory agents had a disadvantage that their use causes a side effect of accompanying gastric ulcer. Having been studying in search of novel anti-inflammatory agents which eliminate such disadvantage, the present inventors have now found the compounds of this invention and thus accomplished the present invention.

The compounds of the present invention have antiphlogistic, analgesic, antipyretic, diuretic and hypotensive activities and therefore can be used for treatment and prevention of various diseases due to inflammation, edama, hypertention, etc.

According to the present invention, the 2-acyl-6-aminomethylphenol derivatives of the formula (I) wherein $R^6$ represents a hydrogen atom and all the other variables are as defined above, i.e., the compounds of the formula:

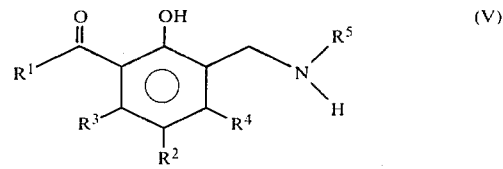

wherein all the variables are as defined above, can be produced by subjecting the 2-acyl-6-aminomethylphenol derivatives in which $R^6$ represents an acyl group, i.e., the compounds of the formula:

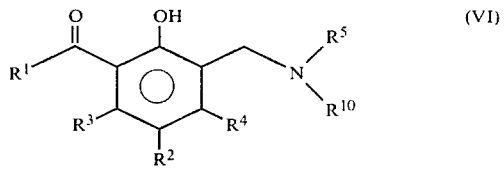

wherein $R^{10}$ represents an acyl group and all the other variables are as defined above, to a reaction for removing the $R^{10}$. This elimination reaction is carried out using an aqueous solution of an inorganic acid such as hydrochloric acid, hydrobromic acid, hydroiodic acid, sulfuric acid, phosphoric acid or nitric acid in a lower alkanol such as methanol or ethanol or acetic acid, preferably in ethanol at a temperature of from room temperature to the refluxing temperature of the solvent, preferably at the refluxing temperature of the solvent. The resulting product may be purified by recrystallization or carbobenzoxylated and then purified by recrystallization or chromatography followed by the removal of the carbobenzoxy group. The resulting product is obtained in the form of its acid addition salt with an inorganic acid. The free amines can be obtained by neutralizing the acid addition salts according to known methods. The inorganic acid addition salts other than that obtained or the organic acid addition salts can be obtained by adding an inorganic or organic acid to the free amines.

The 2-acyl-6-aminomethylphenol derivatives of the formula (VI) can be obtained by reacting a compound of the formula:

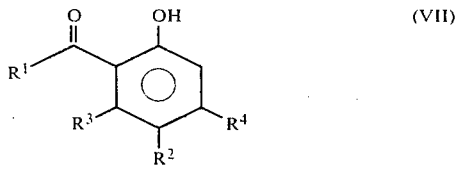

wherein all the variables are as defined above with a compound of the formula:

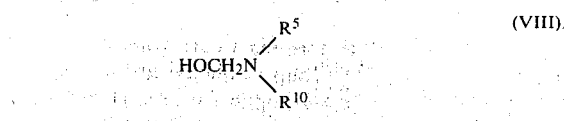

wherein $R^5$ and $R^{10}$ are as defined above. The reaction is carried out in the presence of a strong acid such as hydrochloric acid or sulfuric acid in a lower alkanol such as ethanol or an aliphatic acid such as acetic acid at a temperature of from room temperature to 130° C.

The 2-acyl-6-aminomethylphenol derivatives of the formula (I) wherein $R^6$ represents a lower alkyl group and all the other variables are as defined above, i.e., the compounds of the formula:

(IX)

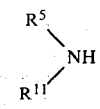

wherein $R^5$ and $R^{11}$ are as defined above and an aqueous solution of formaldehyde, i.e., formalin. The reaction is carried out in the presence or absence of a lower alkanol such as methanol or ethanol, at a temperature of 0° to 50° C., preferably at room temperature. The resulting product may optionally be converted to the acid addition salts according to known methods.

The starting materials of the formula (VII) can be obtained according to the following reaction scheme A or B. All the variables used in the scheme are as defined above.

Reaction Scheme A

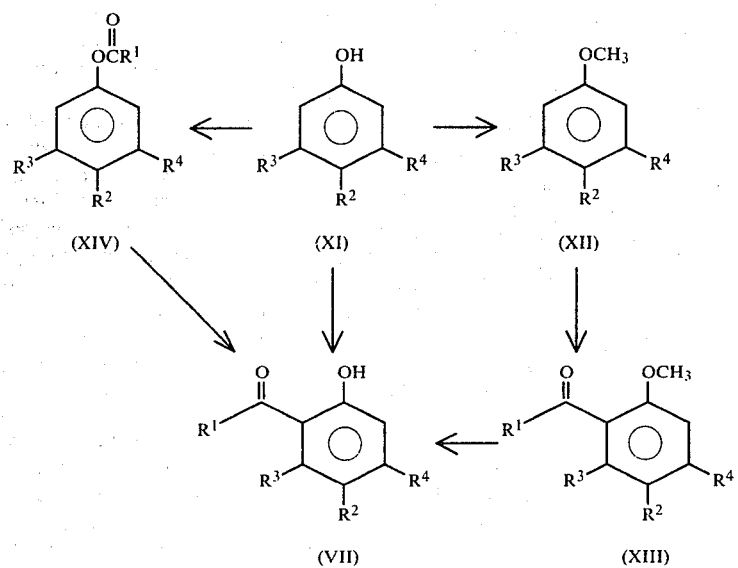

Reaction Scheme B

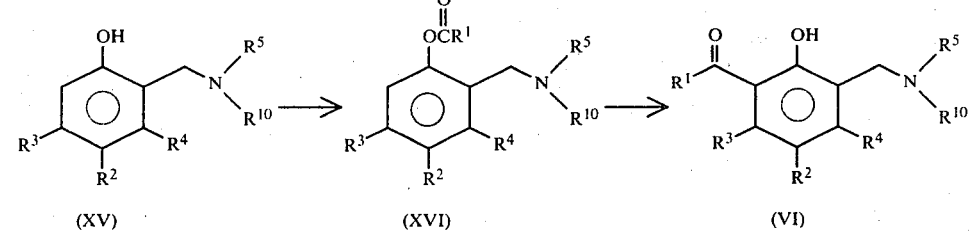

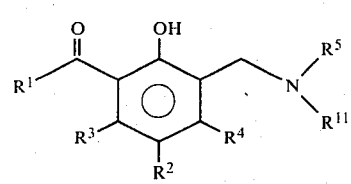

wherein $R^{11}$ represents a lower alkyl group and all the other variables are as defined above can be obtained by reacting a compound of the formula (VII) with an amine of the formula:

To explain the above scheme, the conversion of the compounds of the formula (XI) to the compounds of the formula (XII) can be carried out by known methods such as by etherification by heating with methyl iodide in the presence of potassium carbonate in acetone.

The conversion of the compounds of the formula (XI) to the compounds of the formula (VII) and the conversion of the compounds of the formula (XII) to the compounds of the formula (XIII) can be carried out by known methods, e.g., such as Grignard reaction using metal derivatives, Friedel-Craft reaction or Fries rearrangement. The reactions using metal derivatives like Grignard reaction is conducted by halogenating the phenols or anisoles, converting to the Grignard reagents or lithium compounds and then reacting with the corresponding acylating agent.

The halogenation reaction can be carried out using a halogenating agent such as iodine monochloride, bromine, sulfuryl chloride, etc., in an inert organic solvent such as chloroform, methylene chloride, benzene, etc., or acetic acid at a temperature of room temperature to 100° C.

The conversion to the Grignard reagents or lithium compounds can be carried out by reacting the halogenated compounds with magnesium or an alkyl lithium, for example, butyl lithium in an inert organic solvent such as diethyl ether or tetrahydrofuran at a temperature below room temperature.

The Grignard reagents or lithium compounds are reacted with an acylating agent such as acyl halide, acid or its lower ester in an inert organic solvent such as diethyl ether or tetrahydrofuran at a temperature below room temperature, for example, at 0° C., and oxidation of hydroxyl group, for example, manganese dioxide, in an inert organic solvent such as methylene chloride, diethyl ether, tetrahydrofuran and the like at room temperature to give the compounds of the formula (VII) or (XIII).

The acylation by Friedel-Craft reaction is preferably applied to the anisoles of the formula (XII) because the hydroxyl group of the phenols is often preferentially acylated. The reaction is carried out in an inert organic solvent such as carbon disulfide, nitrobenzene, chloroform, methylene chloride, carbon tetrachloride, petroleum benzine, etc., in the presence of a catalyst such as aluminum chloride, aluminum bromide, tin tetrachloride, iron trichloride, zinc chloride, boron trifluoride, titanium tetrachloride, hydrofluoric acid, sulfuric acid, phosphorus pentoxide, phosphoric acid, polyphosphoric acid, polyphosphoric acid esters, iodine, etc., with an acylating agent such as acyl halides, acid anhydrides, acid esters, acid amides, etc., generally at 0° C. to the refluxing temperature of the solvent. The resulting product is generally a mixture of the phenol of the formula (VII) and the anisole of the formula (XIII) and by controlling the conditions it is possible to produce predominantly anisole of the formula (XIII). The resulting anisole can be converted to the phenol of the formula (VII) by known methods such as by heating at reflux using a mixed solution of hydrobromic acid and hydroiodic acid in acetic acid.

The acylation by Fries rearrangement can be achieved by esterifying the phenol of the formula (XI) using a well known procedure to obtain the compound of the formula (XIV) and then reacting the resulting compound of the formula (XIV) with aluminum chloride, aluminum bromide, tin tetrachloride, zinc chloride, boron trifluoride, titanium tetrachloride and the like in an inert organic solvent such as carbon disulfide, nitrobenzene, chloroform, methylene chloride, 1,2-dichloroethane and the like, at a temperature of about 0° C. to a refluxing temperature of the solvent used to obtain a compound of the formula (VII).

Also, as shown in Reaction Scheme B, the compound of the formula (V) can be obtained by esterifying the compound of the formula (XV) and then subjecting the resulting compound of the formula (XVI) to the Fries rearrangement under the same condition as set forth above.

The acylation of phenols and anisoles are described in details in "Organic Synthetic Chemistry (Yuki Gosei Kagaku) I Reaction I" by Tetsuji Kameya, Nanko-do, pp. 367–379, and reference can be made to this literature.

The compounds of the formula (VII) wherein $R^7$ represents lower alkylthio group or phenyl group substituted with lower alkylthio group in the case when $R^1$ represents such groups in the formula (II) can be obtained by reacting the compounds of the formula (VII) wherein $R^1$ represents alkyl group substituted with monohalogen atom or $R^7$ represents phenyl group substituted with monohalogen atom with a lower alkylthiol in the presence of base such as sodium hydride or sodium methoxide in a lower alkanol such as methanol or a mixed solvent of a lower alkanol and tetrahydrofuran at a temperature of from room temperature to the refluxing temperature of the solvent. The compounds of the formula (VII) wherein $R^7$ represents lower alkylthio group can be converted to the sulfinyl or sulfonyl compounds by known methods.

The phenols of the formula (XI) are known compounds or can be obtained by known methods. For the compounds of the formula (XI) which contain the bicyclo ring set forth in the formula (III) or (IV), reference is invited to Japanese Patent Application No. 158737/77 Specification.

Since the 2-acyl-6-aminomethylphenol derivatives and pharmaceutically acceptable acid addition salts thereof have antiphlogistic, analgesic, antipyretic, diuretic and hypotensive activities, they can be used as anti-inflammatory agents, analgesics, antipyretics, diuretics, micturating agents, and hypotensive agents. For example, in a laboratory experiment, one hour after oral administration with these compounds, the rats were subcutaneously injected with 0.1 ml of 1% carrageenan suspension on the plantar surface of the right hind paw. The swelling was measured at the third hour of carrageenan injection. Anti-inflammatory effect of the compounds was determined as percentage inhibition of the swelling, taking the swelling in the control groups as 100%. The results of the test are shown in Table I.

TABLE I

| Anti-Inflammatory Effect of the Compounds of this Invention on Carrageenan-Induced Edema in Rat Paws | |
|---|---|
| Compound | % Inhibition of Paw Edema 30 mg/kg (%) |
| 2-Acetyl-4-tert-butyl-6-aminomethylphenol hydrochloride | 46.7 |
| 2-Propionyl-4-tert-butyl-6-aminomethylphenol hydrochloride | 72.8 |
| 2-Butyryl-4-tert-butyl-6-aminomethylphenol hydrochloride | 34.1 |
| 2-Isobutyryl-4-tert-butyl-6-aminomethylphenol hydrochloride | 55.5 |
| 2-Chloroacetyl-4-tert-butyl-6-aminomethylphenol hydrochloride | 59.2 |
| 2-(3-methylthiopropionyl)-4-tert-butyl-6-aminomethylphenol hydrochloride | 29.3 |
| 2-Cyclohexylcarbonyl-4-tert-butyl-6-aminomethylphenol hydrochloride | 27.1 |
| 2-Benzoyl-4-tert-butyl-6-aminomethylphenol hydrochloride | 47.6 |
| 2-(4-Bromobenzoyl)-4-tert-butyl-6-aminomethylphenol hydrochloride | 35.0 |
| 2-Phenylacetyl-4-tert-butyl-6-aminomethylphenol hydrochloride | 20.3 |
| 1-Aminomethyl-3-acetyl-5-methyl-5,6,7,8-tetrahydro-2-naphthol hydrochloride | 66.3 |
| 1-Acetyl-3-aminomethyl-5,6,7,8-tetrahydro-2-naphthol hydrochloride | 55.3 |
| 1-Propionyl-3-aminomethyl-5,6,7,8- | 37.4 |

TABLE I-continued

Anti-Inflammatory Effect of the Compounds of this Invention on Carrageenan-Induced Edema in Rat Paws

| Compound | % Inhibition of Paw Edema 30 mg/kg (%) |
|---|---|
| tetrahydro-2-naphthol hydrochloride | |

As will be clear from the results shown in Table 1, the compound of this invention inhibits carrageenan-induced edema well at low dosage levels.

The compounds of this invention also possess an excellent analgesic activity, and the analgesic effects of typical compounds of this invention determined by the acetic acid stretching method and the Randall-Selitto method are shown in Tables II and III, respectively.

(1) Acetic Acid Stretching Method

Male mice were given orally with these compounds and 30 minutes later injected intraperitoneally with 0.1 ml/10 g of 0.6% acetic acid. The number of stretching was countered for 10 minutes from 5 minutes after injection of acetic acid. The value was expressed in the percentage of control.

TABLE II

Analgesic Effect of the Compounds of this Invention in Mice

| Compound | Dose (mg/kg) | % Inhibition (%) |
|---|---|---|
| 2-Propionyl-4-tert-butyl-6-amino- | 10 | 35.3 |
|  | 20 | 61.3 |
| methylphenol hydrochloride | 50 | 85.3 |
| 2-Isobutyryl-4-tert-butyl-6-amino-methylphenol hydrochloride | 50 | 49.7 |

(2) Randall-Selitto Method

Male rats were administered orally with 2-propionyl-4-tert-butyl-6-aminomethylphenol hydrochloride 2 hours after injection of 0.1 ml of 20% suspension beer yeast into subplantar area of one hind paw. Pain threshold determination was made on the normal and inflamed foot, using apparatus similar to that described by Randall-Selitto. Pain threshold change was expressed as percentage of control.

TABLE III

Analgesic Effect of the Compound of this Invention in Rat

| Compound | Dose (mg/kg) | % Inhibition (%) |
|---|---|---|
| 2-Propionyl-4-tert-butyl-6-amino-methylphenol hydrochloride | 50 | 70 |
|  | 100 | 113 |

As is apparent from the results shown in Tables II and III above, the compounds of the present invention exhibit excellent analgesic effect at a low dosage level.

Also, one of the characteristic features of the compounds of this invention is that they do not induce any sign of ulcer upon oral administration. For example, a typical compound of this invention, 2-propionyl-4-tert-butyl-6-aminomethylphenol hydrochloride did not show any sign of ulcer in rats upon oral administration at a dosage level of 200 mg/kg.

Examples of the preferred 2-acyl-6-aminomethylphenol derivatives of the formula (I) include:
2-acetyl-4-tert-butyl-6-aminomethylphenol,
2-propionyl-4-tert-butyl-6-aminomethylphenol,
2-butyryl-4-tert-butyl-6-aminomethylphenol,
2-isobutyryl-4-tert-butyl-6-aminomethylphenol,
2-valeryl-4-tert-butyl-6-aminomethylphenol,
2-chloroacetyl-4-tert-butyl-6-aminomethylphenol,
2-trifluoroacetyl-4-tert-butyl-6-aminomethylphenol,
2-cyclohexylcarbonyl-4-tert-butyl-6-aminomethylphenol,
2-benzoyl-4-tert-butyl-6-aminomethylphenol,
2-(4-bromobenzoyl)-4-tert-butyl-6-aminomethylphenol,
2-(4-methylthiobenzoyl)-4-tert-butyl-6-aminomethylphenol,
2-phenylacetyl-4-tert-butyl-6-aminomethylphenol,
2-(3-methylthiopropionyl)-4-tert-butyl-6-aminomethylphenol,
2-(3-methoxypropionyl)-4-tert-butyl-6-aminomethylphenol,
2-(3-N,N-dimethylaminopropionyl)-4-tert-butyl-6-aminomethylphenol,
2-acetyl-4-phenyl-6-aminomethylphenol,
2-propionyl-4-phenyl-6-aminomethylphenol,
2-butyryl-4-phenyl-6-aminomethylphenol,
2-isobutyryl-4-phenyl-6-aminomethylphenol,
2-valeryl-4-phenyl-6-aminomethylphenol,
2-chloroacetyl-4-phenyl-6-aminomethylphenol,
2-trifluoroacetyl-4-phenyl-6-aminomethylphenol,
2-cyclohexylcarbonyl-4-phenyl-6-aminomethylphenol,
2-benzoyl-4-phenyl-6-aminomethylphenol,
2-(4-bromobenzoyl)-4-phenyl-6-aminomethylphenol,
2-(4-methylthiobenzoyl)-4-phenyl-6-aminomethylphenol,
2-phenylacetyl-4-phenyl-6-aminomethylphenyl,
2-(3-methylthiopropionyl)-4-phenyl-6-aminomethylphenol,
2-(3-methoxypropionyl)-4-phenyl-6-aminomethylphenol,
2-(3-N,N-dimethylpropionyl)-4-phenyl-6-aminomethylphenol,
1-acetyl-3-aminomethyl-5,6,7,8-tetrahydro-2-naphthol,
1-propionyl-3-aminomethyl-5,6,7,8-tetrahydro-2-naphthol,
1-butyryl-3-aminomethyl-5,6,7,8-tetrahydro-2-naphthol,
1-isobutyryl-3-aminomethyl-5,6,7,8-tetrahydro-2-naphthol,
1-valeryl-3-aminomethyl-5,6,7,8-tetrahydro-2-naphthol,
1-chloroacetyl-3-aminomethyl-5,6,7,8-tetrahydro-2-naphthol,
1-trifluoroacetyl-3-aminomethyl-5,6,7,8-tetrahydro-2-naphthol,
1-cyclohexylcarbonyl-3-aminomethyl-5,6,7,8-tetrahydro-2-naphthol,
1-benzoyl-3-aminomethyl-5,6,7,8-tetrahydro-2-naphthol,
1-(4-bromobenzoyl)-3-aminomethyl-5,6,7,8-tetrahydro-2-naphthol,
1-(4-methylthiobenzoyl)-3-aminomethyl-5,6,7,8-tetrahydro-2-naphthol,
1-phenylacetyl-3-aminomethyl-5,6,7,8-tetrahydro-2-naphthol,
1-(3-methylthiopropionyl)-3-aminomethyl-5,6,7,8-tetrahydro-2-naphthol,
1-(3-methoxypropionyl)-3-aminomethyl-5,6,7,8-tetrahydro-2-naphthol,
1-(3-N,N-dimethylaminopropionyl)-3-aminomethyl-5,6,7,8-tetrahydro-2-naphthol,
1-aminomethyl-3-acetyl-5,6,7,8-tetrahydro-2-naphthol, 1-aminomethyl-3-propionyl-5,6,7,8-tetrahydro-2-naphthol,
1-aminomethyl-3-butyryl-5,6,7,8-tetrahydro-2-naphthol,
1-aminomethyl-3-isobutyryl-5,6,7,8-tetrahydro-2-naphthol,
1-aminomethyl-3-valeryl-5,6,7,8-tetrahydro-2-naphthol,
1-aminomethyl-3-chloroacetyl-5,6,7,8-tetrahydro-2-naphthol,
1-aminomethyl-3-trifluoroacetyl-5,6,7,8-tetrahydro-2-naphthol,
1-aminomethyl-3-cyclohexylcarbonyl-5,6,7,8-tetrahydro-2-naphthol,
1-aminomethyl-3-benzoyl-5,6,7,8-tetrahydro-2-naphthol,
1-aminomethyl-3-(4-bromobenzoyl)-5,6,7,8-tetrahydro-2-naphthol,
1-aminomethyl-3-(4-methylthiobenzoyl)-5,6,7,8-tetrahydro-2-naphthol,
1-aminomethyl-3-phenylacetyl-5,6,7,8-tetrahydro-2-naphthol,
1-aminomethyl-3-(3-methylthiopropionyl)-5,6,7,8-tetrahydro-2-naphthol,
1-aminomethyl-3-(3-methoxypropionyl)-5,6,7,8-tetrahydro-2-naphthol,
1-aminomethyl-3-(3-N,N-dimethylaminopropionyl)-5,6,7,8-tetrahydro-2-naphthol,
1-aminomethyl-3-acetyl-5-methyl-5,6,7,8-tetrahydro-2-naphthol,
4-acetyl-6-aminomethyl-5-indanol,
4-propionyl-6-aminomethyl-5-indanol,
4-butyryl-6-aminomethyl-5-indanol,
4-isobutyryl-6-aminomethyl-5-indanol,
4-valeryl-6-aminomethyl-5-indanol,
4-chloroacetyl-6-aminomethyl-5-indanol,
4-trifluoroacetyl-6-aminomethyl-5-indanol,
4-cyclohexylcarbonyl-6-aminomethyl-5-indanol,
4-benzoyl-6-aminomethyl-5-indanol,
4-(4-bromobenzoyl)-6-aminomethyl-5-indanol,
4-(4-methylthiobenzoyl)-6-aminomethyl-5-indanol,
4-phenylacetyl-6-aminomethyl-5-indanol,
4-(3-methylthiopropionyl)-6-aminomethyl-5-indanol,
4-(3-methoxypropionyl)-6-aminomethyl-5-indanol,
4-(3-N,N-dimethylaminopropionyl)-6-aminomethyl-5-indanol,
4-aminomethyl-6-acetyl-5-indanol,
4-aminomethyl-6-propionyl-5-indanol,
4-aminomethyl-6-butyryl-5-indanol,
4-aminomethyl-6-isobutyryl-5-indanol,
4-aminomethyl-6-valeryl-5-indanol,
4-aminomethyl-6-chloroacetyl-5-indanol,
4-aminomethyl-6-trifluoroacetyl-5-indanol,
4-aminomethyl-6-cyclohexylcarbonyl-5-indanol,
4-aminomethyl-6-benzoyl-5-indanol,
4-aminomethyl-6-(4-bromobenzoyl)-5-indanol,
4-aminomethyl-6-(4-methylthiobenzoyl)-5-indanol,
4-aminomethyl-6-phenylacetyl-5-indanol,
4-aminomethyl-6-(3-methylthiopropionyl)-5-indanol,
4-aminomethyl-6-(3-N,N-dimethylaminopropionyl)-5-indanol,
1-acetyl-3-aminomethyl-5,6,7,8-tetrahydro-2-naphthol,
1-propionyl-3-aminomethyl-5,6,7,8-tetrahydro-2-naphthol,
2-nicotinyl-4-tert-butyl-6-aminomethylphenol,
2-propionyl-4-methylthio-6-aminomethylphenol,
their N-methyl-, N,N-dimethyl- and N-chloroacetyl aminophenol derivatives as well as their pharmaceutically acceptable acid addition salts.

The effective administration for the treatment or prevention of various diseases caused by inflammation, edema and hypertension is an oral or parenteral administration and it is desired to administer a unit dosage of 5 to 2,000 mg given once to several times a day. The exact dose, however, is to be determined depending on the age and body weight of the patient, the severity of the disease, the administration route chosen and the number of administration.

Solid dosage forms include tablets, pills, powders and granules. In such solid dosage forms, one or more active materials are mixed with at least one inert diluent such as semidigested starch, potato starch, alginic acid, mannitol or lactose. The dosage forms may contain additives other than diluents, for example, lubricants such as magnesium stearate, according to the standard practice. Liquid dosage forms for oral administration include pharmaceutically acceptable emulsions, solutions, suspensions, syrups and elixirs, and they generally contain common inert diluents such as water and liquid paraffin. The dosage forms contain in addition to the inert diluents, for example, wetting agents, suspending agents, sweetening agents, flavoring agents, perfumes, preservatives or the like. Further, as another oral dosage form, there are included capsules which contain one or more active materials and optionally diluents or excipients, e.g., those made of absorbable materials such as gelatin.

Preparations for parenteral administration contain sterile aqueous or non-aqueous solutions, suspensions or emulsions. Non-aqueous solvents or suspensions include propylene glycol, polyethylene glycol, vegetable oil such as oil and injectable organic acid ester such as ethyl oleate. These dosage forms can contain adjuvants such as preservatives, wetting agents, emulsifiers, dispersing agents, etc. They can be sterilized by the filtration through a bacterial filter, by the incorporation of a bactericide or by the irradiation. Further, sterile solid preparations can be produced for dissolving in a sterile solvent for injection just prior to use.

The present invention is more particularly described in the following Reference Examples and Examples which should not be construed as limiting the scope of the invention. In Reference Examples and Examples, the abbreviations "TLC", "IR", "NMR" and "MS" stand for thin-layer chromatography, infrared absorption spectrum, nuclear magnetic resonance spectrum and mass spectrum, respectively; the proportions of solvents set forth for the separation by chromatography are given in volume, the solvents given in parentheses in "TLC" are eluting solvents, the "IR" is measured by a solution method unless otherwise mentioned and the "NMR" is measured in deuterochloroform (CDCl$_3$) solution unless otherwise mentioned.

REFERENCE EXAMPLE 1

4-tert-Butylanisole

To 15.0 g of 4-tert-butylphenol dissolved in 100 ml of acetone were added 37.5 ml of methyl iodide and 83.0 g of potassium carbonate and heated at reflux for 20 hours. The reaction mixture was filtered and the filtrate was concentrated at reduced pressure. Diethyl ether was added to the residue to remove the insoluble matters by the filtration and the filtrate was concentrated at reduced pressure. The residue was purified by vacuum distillation to give 15.5 g of the title compound having the following physical properties.

b.p.: 63°–64° C./2.0 mmHg

IR: $\nu$=3050, 2960, 2900, 2870, 2830, 1615, 1585, 1515, 1460, 1440, 1395, 1370, 1300, 1250, 1180, 1115, 1040, 830, 795, 660 cm$^{-1}$.

NMR: $\delta$=7.08 (2H, d, J=9 Hz), 6.62 (2H, d, J=9 Hz), 3.67 (3H, s), 1.27 (9H, s).

In a similar manner, a compound having the following physical properties was obtained from 2-iodo-4-tert-butylphenol (the compound described in Example 8 of Japanese Patent Laid Open No. 13224/72 Specification).

(a) 2-Iodo-4-tert-butylanisole

Yield: 74% m.p.: 115°–120° C./2.0 mmHg.

REFERENCE EXAMPLE 2

2-Acetyl-4-tert-butylphenol

To 7.40 g of aluminum chloride suspended in 100 ml of methylene chloride were added, under nitrogen, 8.20 g of 4-tert-butylanisole (prepared in Reference Example 1) dissolved in 50 ml of methylene chloride at 0° C. followed by dropwise addition of 3.92 ml of acetyl chloride dissolved in 50 ml of methylene chloride at the same temperature. The mixture was stirred at 20° C. for 30 minutes. The reaction mixture was concentrated at reduced pressure and poured into 200 ml of ice-water and extracted with diethyl ether. The extract was washed with water and saturated brine successively, dried over magnesium sulfate anhydride and concentrated at reduced pressure. The residue was chromatographed on silica gel column using a mixed solvent of methylene chloride and cyclohexane (1:2) as an eluting agent to give 5.30 g of the title compound and 3.79 g of 2-acetyl-4-tert-butylanisole. The physical properties of each compound are as follows.

2-Acetyl-4-tert-butylphenol.

TLC (methylene chloride): Rf=0.60.

IR: $\nu$=2960, 1770, 1645, 1620, 1595, 1490, 1370, 1330, 1310, 1270, 1250, 1230, 1200, 1120, 1070, 1030, 960, 890, 860, 825, 790, 640 cm$^{-1}$.

NMR: $\delta$=12.10 (1H, s), 7.60-7.25 (2H, m), 6.74 (1H, d, J=9 Hz), 2.57 (3H, s), 1.27 (9H, s).

° 2-Acetyl-4-tert-butylanisole.

TLC (methylene chloride): Rf=0.44.

IR: $\nu$=2960, 1675, 1610, 1575, 1500, 1460, 1440, 1400, 1370, 1305, 1295, 1270, 1255, 1235, 1180, 1150, 1070, 1020, 980, 910, 820 cm$^{-1}$.

NMR: $\delta$=7.57 (1H, d, J=2.5 Hz), 7.30 (1H, dd, J=9 Hz and 2.5 Hz), 6.70 (1H, d, J=9 Hz), 3.77 (3H, s), 2.53 (3H, s), 1.27 (9H, s).

In a similar manner, the following compounds were obtained from the corresponding acyl chloride and 4-tert-butylanisole.

(a) 2-Cyclohexylcarbonyl-4-tert-butylanisole

Yield: 65%.

TLC (methylene chloride:cyclohexane=1:1): Rf=0.32.

IR: $\nu$=2960, 2930, 2850, 1670, 1605, 1580, 1495, 1460, 1450, 1400, 1370, 1295, 1270, 1255, 1200, 1180, 1150, 1130, 1110, 1030, 990, 895, 820 cm$^{-1}$.

NMR (CCl$_4$ solution): $\delta$=7.40-7.03 (2H, m), 6.60 (1H, d, J=8 Hz), 3.77 (3H, s), 3.40-2.73 (1H, broad s), 2.20-1.10 (10H, m), 1.30 (9H, s).

(b) 2-Benzoyl-4-tert-butylanisole

Yield: 62%.

TLC (methylene chloride:cyclohexane=1:1): Rf=0.16.

IR: $\nu$=3060, 2960, 2900, 2870, 1660, 1610, 1600, 1580, 1500, 1460, 1450, 1405, 1370, 1320, 1275, 1255, 1205, 1180, 1170, 1135, 1110, 1075, 1030, 970, 900, 855, 820, 810, 750, 730, 710, 690, 670, 640 cm$^{-1}$.

NMR (CCl$_4$ solution): $\delta$=7.77-7.17 (7H, m), 6.71 (1H, d, J=9 Hz) 3.57 (3H, s), 1.30 (9H, s).

(c) 2-(4-Bromobenzoyl)-4-tert-butylanisole

Yield: 48%.

TLC (methylene chloride:cyclohexane=1:1): Rf=0.20.

IR: $\nu$=2960, 1660, 1610, 1585, 1570, 1500, 1480, 1460, 1405, 1365, 1310, 1270, 1255, 1180, 1165, 1130, 1100, 1070, 1030, 1010, 970, 855, 820, 770, 735 cm$^{-1}$.

NMR: $\delta$=7.70-7.20 (6H, m), 6.77 (1H, d, J=9 Hz), 3.62 (3H, s), 1.30 (9H, s).

(d) 2-Propionyl-4-tert-butylanisole

Yield: 40.3%.

m.p.: 40°–41° C. (white crystals, not recrystallized).

IR (KBr disc.): $\nu$=3040, 2965, 2945, 2900, 2875, 2845, 1670, 1610, 1580, 1500, 1460, 1410, 1400, 1370, 1300, 1270, 1210, 1190, 1180, 1140, 1110, 1080, 1040, 1030, 980, 870, 820, 815, 675, 620, 540 cm$^{-1}$.

NMR: $\delta$=7.57 (1H, d, J=2 Hz), 7.37 (1H, dd, J=2 Hz), 6.85 (1H, d, J=9 Hz), 3.83 (3H, s), 3.00 (2H, q, J=8 Hz), 1.29 (9H, s), 1.17 (3H, t, J=8 Hz).

MS: m/e=220 (M+), 205, 191.

TLC (cyclohexane:ethylacetate=9:1): Rf=0.60.

(e) 2-Phenylacetyl-4-tert-butylanisole

Yield: 100% (not purified by column chromatography).

IR: $\nu$=3080, 3050, 2950, 2920, 2875, 1810, 1680, 1605, 1500, 1470, 1455, 1405, 1370, 1275, 1260, 1190 cm$^{-1}$.

NMR: $\delta$=7.95 (1H, d, J=3 Hz), 7.37 (1H, dd), 7.15 (5H, s), 6.77 (1H, d, J=9 Hz), 4.28 (2H, s), 3.80 (3H, s), 1.27 (9H, s).

(f) ° 2-Chloroacetyl-4-tert-butylphenol

Yield: 10%.

m.p.: 51°–52° C. (not recrystallized).

TLC (methylene chloride:cyclohexane=1:2): Rf=0.22.

IR (KBr disc.): $\nu$=3450, 3075, 2975, 2920, 2880, 1780, 1640, 1625, 1595, 1495, 1490, 1405, 1375, 1265, 1195, 1050, 760 cm$^{-1}$.

NMR: $\delta$=7.55-6.72 (4H, m), 4.65 (2H, s), 1.32 (9H, s).

° 2-Chloroacetyl-4-tert-butylanisole.

Yield: 6.6%.

NMR: $\delta$=7.85-6.73 (3H, m), 4.72 (2H, s), 3.87 (3H, s), 1.30 (9H, s).

(g) 2-Valeryl-4-tert-butylanisole

Yield: 100% (not purified by column chromatography).

TLC (cyclohexane:methylene chloride=1:1): Rf=0.38.

(h) 2-Butyryl-4-tert-butylanisole

Yield: 85%.

TLC (cyclohexane:methylene chloride=1:1): Rf=0.51

NMR (CCl$_4$ solution): δ=7.50 (1H, d, J=3 Hz), 7.29 (1H, dd, J=9 Hz and 3 Hz) 6.70 (1H, d, J=9 Hz), 3.85 (3H, s), 2.85 (2H, t), 1.70 (2H, m), 1.35 (9H, s), 0.95 (3H, t).

(i) 2-Isobutyryl-4-butylanisole

Yield: 58%.

TLC (cyclohexane:methylene chloride=1:1): RF=0.51

NMR (CCl$_4$ solution): δ=7.37 (1H, d, J=3 Hz), 7.25 (1H, dd, J=9 Hz and 3 Hz), 6.65 (1H, d, J=9 Hz), 3.77 (3H, s), 3.35 (1H, m), 1.28 (9H, s), 1.05 (6H, d).

(j) 2-(3-Bromopropionyl)-tert-butylanisole

Yield: 55.9%.

m.p.: 125°–126° C. (white needles, not recrystallized).
TLC (cyclohexane:ethyl acetate=9:1): Rf=0.40

(k) 3-Acetyl-5-methyl-5,6,7,8-tetrahydro-2-naphthol

Yield: 55.9%.

TLC (methylene chloride): Rf=0.63.
IR: ν=3400, 2940, 2860, 1765, 1640, 1620, 1580, 1490, 1460, 1425, 1370, 1340, 1310, 1270, 1230, 1170, 1140, 1065, 1020, 960, 895, 780 cm$^{-1}$.
NMR: δ=11.80 (1H, s), 7.38 (1H, s), 6.55 (1H, s), 3.10-2.50 (3H, m), 2.55 (3H, s), 2.2-1.4 (4H, m), 1.27 (3H, d, J=7 Hz).

REFERENCE EXAMPLE 3

2-Cyclohexylcarbonyl-4-tert-butylphenol

To 1.70 g of 2-cyclohexylcarbonyl-4-tert-butylanisole [prepared in Reference Example 2 (a)] dissolved in 10 ml of glacial acetic acid were added 1.0 ml of 57% hydroiodic acid and 2.0 ml of 47% hydrobromic acid, and heated at reflux for 2 hours. The reaction mixture was poured into 50 ml of ice-water, extracted with diethyl ether, and the extract was washed with saturated aqueous sodium thiosulfate solution, water and saturated brine successively, dried over magnesium sulfate anhydride and concentrated at reduced pressure. The residue was chromatographed on silica gel column using a mixed solvent of methylene chloride and cyclohexane (1:2) as an eluting agent to give 1.54 g of the title compound having the following physical properties.

TLC (methylene chloride:cyclohexane=1:1): Rf=0.50

IR: ν=2940, 2860, 1640, 1615, 1490, 1450, 1370, 1340, 1300, 1290, 1270, 1250, 1240, 1190, 1170, 980, 830, 800, 725, 660 cm$^{-1}$.

NMR (CCl$_4$ solution): δ=12.13 (1H, s), 7.52 (1H, d, J=2 Hz), 7.30 (1H, dd, J=9 Hz and 2 Hz), 6.70 (1H, d, J=9 Hz), 3.40-2.90 (1H, broad s), 2.30-1.20 (10OH, m), 1.30 (9H, s).

In a similar manner, the compounds having the following properties were obtained from the corresponding anisoles.

(a) 2-Benzoyl-4-tert-butylphenol

Starting material: 2-benzoyl-4-tert-butylanisole[described in Reference Example 2(b)].

Yield: 89%.

TLC (methylene chloride:cyclohexane=1:1): Rf=0.30.

IR: ν=3200, 3060, 2960, 2900, 2860, 1690, 1630, 1600, 1580, 1480, 1460, 1445, 1400, 1370, 1340, 1300, 1270, 1250, 1230, 1200, 1180, 1160, 1130, 1110, 1080, 1030, 1000, 960, 910, 870, 840, 825, 765, 720, 700, 680, 660, 595 cm$^{-1}$.

NMR (CCl$_4$ solution): δ=11.0 (1H, s), 7.77-7.07 (7H, m), 6.69 (1H, d, J=9 Hz), 1.20 (9H, s).

(b) 2-(4-Bromobenzoyl)-4-tert-butylphenol

Starting material: 2-(4-bromobenzoyl)-4-tert-butylanisole [described in Reference Example 2(c)].

Yield: 87%.

m.p.: 83°–85° C. (not recrystallized).

TLC (methylene chloride:cyclohexane=1:1): Rf=0.45.

IR (KBr disc.): ν=3100, 2950, 2860, 1630, 1600, 1590, 1560, 1480, 1395, 1360, 1340, 1300, 1270, 1250, 1230, 1200, 1170, 1160, 1120, 1105, 1070, 1010, 960, 900, 865, 845, 830, 780, 760, 730, 710, 685, 660, 595, 565, 510, 470, 445, 415 cm$^{-1}$.

NMR: δ=11.57 (1H, s), 7.70-7.30 (6H, m), 6.90 (1H, d, J=9 Hz), 1.27 (9H, s).

(c) 2-Propionyl-4-tert-butylphenol

Starting material: 2-propionyl-4-tert-butylanisole [described in Reference Example 2(d)].

Yield: 69.6%.

TLC (cyclohexane:ethyl acetate=9:1): Rf=0.80.

IR: ν=3060, 2980, 2960, 2930, 2880, 1730, 1650, 1620, 1490, 1460, 1375, 1360, 1300, 1275, 1250, 1220, 1200, 1020, 975, 880, 840, 825 cm$^{-1}$.

NMR (CCl$_4$ solution): δ=7.50 (1H, d, J=2 Hz), 7.46 (1H, dd, J=2 Hz and 8 Hz), 6.85 (1H, d, J=8 Hz), 2.95 (2H, q, J=7 Hz), 2.30 (9H, s), 1.19 (3H, t, J=7 Hz).

(d) 2-Phenylacetyl-4-tert-butylphenol

Starting material: 2-phenylacetyl-4-tert-butylanisole [described in Reference Example 2(e)].

Yield: 63.2%.

TLC (cyclohexane:ethyl acetate=4:1): Rf=0.63

IR: ν=3440, 3050, 2970, 2875, 1740, 1645, 1490, 1370, 1270 cm$^{-1}$.

NMR: δ=7.72 (1H, d, J=2 Hz), 7.40 (1H, dd, J=2 Hz and 9 Hz), 7.20 (5H, s), 6.80 (1H, d, J=9 Hz), 4.22 (2H, s), 1.28 (9H, s).

(e) 2-Valeryl-4-tert-butylphenol

Starting material: 2-valeryl-4-tert-butylanisole [described in Reference Example 2(g)].

Yield: 45%.

TLC (methylene chloride:cyclohexane=1:1): Rf=0.45.

IR: ν=3500-2200, 1950, 1850, 1720, 1640, 1610, 1580, 1480, 1460, 1360, 1290, 1260, 1230, 1180, 1100, 1010, 980, 840, 820, 780 cm$^{-1}$.

NMR (CCl$_4$ solution): δ=11.85 (1H, broad s), 7.55 (1H, d, J=3 Hz), 7.35 (1H, dd, J=9 Hz and 3 Hz), 6.70 (1H, d, J=9 Hz), 2.90 (2H, t), 2.00-1.20 (13H, m), 0.95 (3H, t).

(f) 2-Butyryl-4-tert-butylphenol

Starting material: 2-butyryl-4-tert-butylanisole [described in Reference Example 2(h)].

Yield: 81%.

TLC (methylene chloride:cyclohexane=1:1): Rf=0.53.

NMR (CCl$_4$ solution): δ=11.96 (1H, s), 7.55 (1H, d, J=2.5 Hz), 7.35 (1H, dd, J=9 Hz and 2.5 Hz), 6.73 (1H, d, J=9 Hz), 2.95 (2H, t), 1.75 (2H, m), 1.30 (9H, s), 1.00 (3H, t).

(g) 2-Isobutyryl-4-tert-butylphenol

Starting material: 2-isobutyryl-4-tert-butylanisole [described in Reference Example 2(i)].

Yield: 86%.

TLC (methylene chloride:cyclohexane=1:1): Rf=0.67.

IR: $\nu=3400$-2500, 3080, 2950, 2850, 1740, 1720, 1590, 1490, 1470, 1380, 1360, 1300, 1260, 1240, 1210, 1190, 1160, 1010, 990, 840, 820, 800, 760 cm$^{-1}$.

NMR (CCl$_4$ solution): $\delta=11.95$ (1H, s), 7.65 (1H, d, J=3 Hz), 7.35 (1H, dd, J=9 Hz and 3 Hz), 6.72 (1H, d, J=9 Hz), 3.52 (1H, m), 1.30 (9H, s), 1.25 (6H, d).

(h) 2-(3-Bromopropionyl)-4-tert-butylphenol

Starting material: 2-(3-bromopropionyl)-4-tert-butylanisole [described in Reference Example 2(j)].

Yield: 75.2%.

TLC (cyclohexane:ethyl acetate=9:1): Rf=0.47.

IR: $\nu=3060$, 3040, 2970, 2910, 2870, 1640, 1590, 1480, 1410, 1370, 1300, 1270, 1245, 1200, 1010, 990, 840, 830 cm$^{-1}$.

NMR (CCl$_4$ solution): $\delta=11.57$ (1H, s) 7.53 (1H, d, J=2.5 Hz), 7.36 (1H, dd, J=9 Hz and 2.5 Hz), 6.79 (1H, d, J=9 Hz), 3.57 (4H, m), 1.30 (9H, s).

MS: m/e=286 and 284 (M$^+$), 271, 269, 205, 204, 190, 189, 177, 161.

(i) 2-Trifluoroacetyl-4-tert-butylphenol

Starting material: 2-trifluoroacetyl-4-tert-butylanisole [described in Reference Example 6 below].

Yield: 70%.

TLC (methylene chloride:cyclohexane=1:2): Rf=0.52.

IR: $\nu=3200$, 2960, 1665, 1630, 1580, 1490, 1400, 1370, 1280, 1265, 1235, 1205, 1165, 1150, 970, 870, 840, 820, 790, 720, 660, 590 cm$^{-1}$.

NMR (CCl$_4$ solution): $\delta=1.86$ (1H, s), 7.76 (1H, t, J=2.5 Hz), 7.14 (1H, dd, J=8.5 Hz and 2.5 Hz), 6.97 (1H, d, J=8.5 Hz), 1.32 (9H, s).

MS: m/e=246 (M$^+$), 231, 203, 191, 183, 177, 161, 134.

REFERENCE EXAMPLE 4

2-(4-Methylthiobenzoyl)-4-tert-butylphenol

To a sodium methoxide solution (prepared from 15 ml of methanol and 0.35 g of metal sodium at 30°-40° C.) were added 2.40 ml of 30% methylmercaptan in methanol and stirred at room temperature for 20 minutes. To this solution were added dropwise 1.67 g of 2-(4-bromobenzoyl)-4-tert-butylphenol [prepared in Reference Example 3(b)] dissolved in 5 ml of methanol and heated at reflux for 4 days. The reaction mixture was acidified with 1 N hydrochloric acid and concentrated at reduced pressure. The residue was dissolved in diethyl ether, washed with water and saturated brine successively, dried over magnesium sulfate anhydride, and concentrated at reduced pressure. The residue was chromatographed on silica gel column using a mixed solvent of methylene chloride and cyclohexane (1:2) as an eluting agent to give 0.51 g of the title compound having the following physical properties as yellow crystals.

m.p.: 130°-104° C.

TLC (methylene chloride:cyclohexane=1:2): Rf=0.22.

IR (KBr disc.): $\nu=3050$, 2960, 1630, 1590, 1550, 1480, 1435, 1400, 1370, 1340, 1300, 1270, 1250, 1230, 1205, 1190, 1155, 1125, 1105, 1085, 1005, 955, 905, 865, 850, 835, 820, 785, 760, 745, 725, 695, 655, 590, 525, 510, 480, 450 cm$^{-1}$.

NMR: $\delta=11.60$ (1H, s), 7.70-6.80 (7H, m), 2.50 (3H, s), 1.27 (9H, s).

REFERENCE EXAMPLE 5

2-(3-Methylthiopropionyl)-4-tert-butylphenol

To a mixed solution of 1.65 g of sodium hydride (content 63%) and 15 ml of methanol were added 7.2 ml of 30% methylmercaptan in methanol and stirred at room temperature for 15 minutes. The solution was added dropwise to 4.289 g of 2-(3-bromopropionyl)-4-tert-butylphenol [described in Reference Example 3(h)] dissolved in 37.6 ml of tetrahydrofuran at room temperature and stirred at the same temperature for one hour. The reaction mixture was acidified with 1 N hydrochloric acid and extracted with ethyl acetate. The extract was washed with water, and saturated brine successively, dried over sodium sulfate anhydride and concentrated at reduced pressure. The residue was chromatographed on silica gel column using a mixed solvent of cyclohexane and ethyl acetate (30:1) as an eluting agent to give 2.304 g of the title compound of the following physical properties as pale yellow oil.

TLC (cyclohexane:ethyl acetate=9:1): Rf=0.45

Ir: $\nu=3400$, 3060, 3040, 2960, 2920, 2870, 1615, 1600, 1590, 1482, 1365, 1295, 1265, 1250, 1180 cm$^{-1}$.

NMR (CCl$_4$ solution): $\delta=11.70$ (1H, s), 7.53 (1H, d, J=2 Hz), 7.33 (1H, dd, J=8 Hz and 2 Hz), 6.77 (1H, d, J=8 Hz) 3.40-3.03 (2H, m), 2.93-2.60 (2H, m), 2.10 (3H, s), 1.30 (9H, s).

MS: m/e=252 (M$^+$), 234, 205, 189, 177, 161.

REFERENCE EXAMPLE 6

2-Trifluoroacetyl-4-tert-butylanisole

To 0.73 g of magnesium suspended in 5 ml of diethyl ether were added dropwise, under nitrogen, 8.70 g of 2-iodo-4-tert-butylanisole [described in Reference Example 1(a)] dissolved in 15 ml of diethyl ether and heated at reflux for one hour. To this solution were added dropwise 0.74 ml of trifluoroacetic acid dissolved in 3 ml of diethyl ether at room temperature, and heated at reflux for 1.5 hours. The reaction mixture was poured into ice-water, acidified with conc. sulfuric acid and extracted with diethyl ether. The extract was washed with water and saturated brine successively, dried over magnesium sulfate anhydride and concentrated at reduced pressure. The residue was chromatographed on silica gel column using a mixed solvent of methylene chloride and cyclohexane (1:2) as an eluting agent to give 1.83 g of the title compound having the following physical properties as pale yellow oil.

TLC (methylene chloride:cyclohexane=1:2): Rf=0.55

IR: $\nu=2960$, 2900, 2870, 1715, 1610, 1580, 1500, 1460, 1440, 1410, 1370, 1290, 1270, 1180, 1160, 1110, 1025, 980, 960, 855, 825, 785, 750, 675 cm$^{-1}$.

NMR (CCl$_4$ solution): $\delta=7.60$-7.33 (2H, m), 6.80 (1H, d, J=9 Hz), 3.83 (3H, s), 1.30 (9H, s).

MS: m/e=260 (M$^+$), 245, 217, 205, 191, 175, 148, 133.

REFERENCE EXAMPLE 7

2-Propionyl-4-tert-butylphenol 28 g of 4-tert-butylphenylpropionate was dissolved in 70 ml of nitrobenzene and 30 ml (51.8 g) of titanium tetrachloride was added dropwise to the solution. After completion of the addition, the mixture was stirred at 50° C. for 5 hours and then poured into 100 ml of ice water. The resulting mixture was extracted with diethyl ether, and the ether layer was washed successively with water and an aqueous sodium chloride solution, dried and the solvent was removed. After distilling off nitrobenzene, the residue was distilled to obtain 26 g of the title compound having a boiling point of 119°–122° C./6 mm Hg.

TLC, IR and NMR spectra of the product were found to be the same as set forth in Reference Example 3(c).

EXAMPLE 1

2-Acetyl-4-tert-butyl-6-(N-chloroacetylaminomethyl)-phenol

To 2.88 g of 2-acetyl-4-tert-butylphenol (prepared in Reference Example 2) dissolved in 20 ml of a mixed solution of glacial acetic acid and conc. sulfuric acid (10:1) were added 2.78 g of N-hydroxymethylchloroacetamide at room temperature and stirred at 60° C. for 2 hours. The reaction mixture was poured into 100 ml of ice-water, extracted with diethyl ether and the extract was washed with water and saturated brine successively, dried over magnesium sulfate anhydride and concentrated at reduced pressure. The residue was chromatographed on silica gel column using a mixed solvent of methylene chloride and ethyl acetate (50:1) as an eluting agent to give 3.83 g of the title compound having the following physical properties.

TLC (methylene chloride:ethyl acetate = 10:1): Rf = 0.60.

IR: $\nu$ = 3300, 3080, 2960, 2870, 1740, 1680-1640, 1540, 1460, 1370, 1330, 1280, 1245, 1150, 1120, 1030, 980, 930, 885, 825, 790, 650 cm$^{-1}$.

NMR: $\delta$ = 12.50 (1H, s), 7.57 (1H, d, J = 2.5 Hz), 7.45 (1H, d, J = 2.5 Hz), 7.20 (1H, broad s), 4.48 (2H, d, J = 6 Hz), 4.00 (2H, s), 2.63 (3H, s), 1.30 (9H, s).

In a similar manner, the compounds having the following physical properties were obtained from the corresponding phenols.

(a) 2-Cyclohexylcarbonyl-4-tert-butyl-6-(N-chloroacetylaminomethyl)phenol

Starting material: 2-cyclohexylcarbonyl-4-tert-butylphenol (described in Reference Example 3).

Yield: 62%.

TLC (methylene chloride): Rf = 0.20.

IR (CHCl$_3$ solution): $\nu$ = 3420, 2950, 2860, 1670, 1635, 1530, 1450, 1410, 1370, 1340, 1275, 1245, 1140, 1080 cm$^{-1}$.

NMR (CCl$_4$ solution): $\delta$ = 12.77 (1H, s), 7.47 (1H, d, J = 2 Hz), 7.37 (1H, d, J = 2 Hz), 7.30-6.90 (1H, broad s), 4.33 (2H, d, J = 2 Hz), 3.85 (2H, s), 3.40-3.00 (1H, broad s), 2.20-1.20 (10H, m), 1.31 (9H, s).

(b) 2-Benzoyl-4-tert-butyl-6-(N-chloroacetylaminomethyl)phenol

Starting material: 2-benzoyl-4-tert-butylphenol [described in Reference Example 3(a)].

Yield: 78%.

TLC (methylene chloride): Rf = 0.20.

NMR: $\delta$ = 12.20 (1H, s), 7.70-7.10 (8H, m), 4.50 (2H, d, J = 6Hz), 3.98 (2H, s), 1.20 (9H, s).

(c) 2-(4-Bromobenzoyl)-4-tert-butyl-6-(N-chloroacetylaminomethyl)phenol

Starting material: 2-(4-bromobenzoyl)-4-tert-butylphenol [described in Reference Example 3(b)].

Yield: 63%.

m.p.: 52°–55° C. (not recrystallized).

IR (KBr disc.): $\nu$ = 3300, 3060, 2960, 1660, 1625, 1590, 1530, 1450, 1395, 1370, 1340, 1275, 1250, 1180, 1070, 995, 830, 790 cm$^{-1}$.

NMR: $\delta$ = 7.70-7.07 (8H, m), 4.48 (2H, d, J = 6 Hz), 3.97 (2H, s), 1.23 (9H, s).

MS: m/e = 438, 423, 403, 361, 330, 204, 189, 183, 173, 155.

(d) 2-Propionyl-4-tert-butyl-6-(N-chloroacetylaminomethyl)phenol

Starting material: 2-propionyl-4-tert-butylphenol [described in Reference Example 3(c)].

Yield: 65.3%.

TLC (cyclohexane:ethyl acetate = 4:1): Rf = 0.25.

IR: $\nu$ = 3290, 3080, 3050, 2960, 2900, 2870, 1660, 1640, 1540, 1530, 1455, 1365, 1270, 1230, 1100, 820 cm$^{-1}$.

NMR (CCl$_4$ solution): $\delta$ = 12.5 (1H, s), 7.50 (1H, d, J = 2 Hz), 7.39 (1H, d, J = 2 Hz), 7.35-7.00 (1H, broad s), 4.35 (2H, d, J = 6 Hz), 3.86 (2H, d), 2.97 (2H, q, J = 8 Hz), 1.29 (9H, s), 1.22 (3H, t, J = 8 Hz).

MS: m/e = 311 (M+), 276, 246, 234, 218, 203, 189, 162, 161.

(e) 2-Phenylacetyl-4-tert-butyl-6-(N-chloroacetylaminomethyl)phenol

Starting material: 2-phenylacetyl-4-tert-butylphenol [described in Reference Example 3(d)].

Yield: 57.9%.

TLC (ethyl acetate:cyclohexane = 1:2): Rf = 0.34.

IR: $\nu$ = 3425, 3300, 3075, 3045, 2975, 2945, 1670, 1640, 1535, 1455, 1370, 1280, 1250, 1230, 1080 cm$^{-1}$.

NMR: $\delta$ = 7.72 (1H, d, J = 2 Hz), 7.45 (1H, d, J = 2 Hz), 7.23 (5H, s), 4.45 (2H, d, J = 6 Hz), 4.27 (2H, s), 3.98 (2H, s), 1.30 (9H, s).

(f) 2-Chloroacetyl-4-tert-butyl-6-(N-chloroacetylaminomethyl)phenol

Starting material: 2-chloroacetyl-4-tert-butylphenol [described in Reference Example 2(f)].

Yield: 24.6%.

IR: $\nu$ = 3400, 3300, 2940, 2860, 2800-2100, 1735, 1710, 1660, 1535, 1455, 1370, 1330, 1225, 1205, 1000 cm$^{-1}$.

NMR: $\delta$ = 7.77-7.37 (3H, m), 7.37-6.97 (1H, broad s), 4.65 (2H, s), 4.47 (2H, d, J = 6 Hz) 3.97 (2H, s), 1.30 (9H, s).

(g)
2-(4-Methylthiobenzoyl)-4-tert-butyl-6-(N-chloroacetylaminomethyl)phenol Starting material: 2-(4-methylthiobenzoyl)-4-tert-butylphenol [described in Reference Example 4].
Yield: 54%.
m.p.: 154°–157° C. (not recrystallized).
IR (KBr disc.): $\nu=3400, 3270, 3080, 2970, 1680, 1625, 1600, 1555, 1460, 1405, 1375, 1345, 1320, 1290, 1255, 1190, 1100, 1045, 1010, 850, 800, 670, 620, 595, 510$ cm$^{-1}$.
NMR: $\delta=7.90\text{-}7.06$ (7H, m), 4.52 (2H, d, J=6Hz), 4.02 (2H, s), 2.53 (3H, s), 1.25 (9H, s).

(h)
2-Valeryl-4-tert-butyl-6-(N-chloroacetylaminomethyl)-phenol

Starting material: 2-valeryl-4-tert-butylphenol [described in Reference Example 3(e)].
Yield: 60%
TLC (methylene chloride): Rf=0.26.
IR: $\nu=3300, 3050, 2950, 2850, 1670, 1640, 1540, 1480, 1370, 1270, 1220, 1080, 1050, 830, 790, 770, 740$ cm$^{-1}$.
NMR (CCl$_4$ solution): $\delta=12.40$ (1H, s), 7.50 (1H, d, J=3Hz), 7.40 (1H, d, J=3Hz), 7.40-6.70 (1H, broad s), 4.40 (2H, d), 3.90 (2H, s), 2.90 (2H, t), 1.30 (9H, s), 0.95 (3H, t).

(i)
2-Butyryl-4-tert-butyl-6-(N-chloroacetylaminomethyl)-phenol

Starting material: 2-butyryl-4-tert-butylphenol [described in Reference Example 3(f)].
Yield: 82%.
TLC (methylene chloride): Rf=0.29.
NMR (CCl$_4$ solution): $\delta=12.50$ (1H, s), 7.52 (1H, d, J=2.5Hz), 7.42 (1H, d, J=2.5Hz), 7.42-6.70 (1H, broad s), 4.35 (2H, d), 3.87 (2H, s), 2.92 (2H, t), 2.05-1.50 (2H, m), 1.30 (9H, s), 1.05 (3H, t).

(j)
2-Isobutyryl-4-tert-butyl-6-(N-chloroacetylaminomethyl)phenol

Starting material: 2-isobutyryl-4-tert-butylphenol [described in Reference Example 3(g)].
Yield: 69%.
TLC (methylene chloride): Rf=0.42.
IR: $\nu=3420, 3300, 3080, 2950, 2850, 1680, 1640, 1610, 1530, 1470, 1370, 1280, 1240, 1070, 790, 770$ cm$^{-1}$.
NMR (CCl$_4$ solution): $\delta=12.50$ (1H, s), 7.53 (1H, d, J=2.5Hz) 7.39 (1H, d, J=2.5Hz), 7.30-6.70 (1H, broad s), 4.32 (2H, d), 3.85 (2H, s), 3.50 (1H, m), 1.30 (9H, s), 1.25 (6H, d).

(k)
2-(3-Methylthiopropionyl)-4-tert-butyl-6-(N-chloroacetylaminomethyl)phenol Starting material: 2-(3-methylthiopropionyl)-4-tert-butylphenol [described in Reference Example 5].
Yield: 41.1%.
TLC (cyclohexane:ethyl acetate=4:1): Rf=0.24.
IR: $\nu=3275, 3070, 2960, 2910, 2860, 1675, 1640, 1575, 1410, 1370, 1275, 1240, 850, 810, 735$ cm$^{-1}$.
NMR: $\delta=7.60$ (1H, d), 7.50 (1H, d), 4.50 (2H, d), 4.00 (2H, s), 3.50-3.17 (2H, m), 3.03-2.66 (2H, m), 3.17 (3H, s), 1.33 (9H, s).
MS: m/e=357 (M$^+$), 339, 322, 310, 294, 274, 246, 232, 217, 201, 189.

(l)
2-Trifluoroacetyl-4-tert-butyl-6-(N-chloroacetylaminomethyl)phenol

Starting material: 2-trifluoroacetyl-4-tert-butylphenol [described in Reference Example 3(i)].
Yield: 32%.
TLC (methylene chloride:cyclohexane=2:1): RF=0.12.
IR: $\nu=3270, 2960, 1740, 1665, 1535, 1460, 1370, 1270, 1205, 1150, 1045, 1010, 840, 795, 720$ cm$^{-1}$.
NMR (CCl$_4$ solution): $\delta=7.83\text{-}7.67$ (2H, m), 7.25 (1H, broad s), 4.47 (2H, d, J=6.5Hz), 3.96 (2H, s), 1.33 (9H, s).
MS: m/e=351 (M$^+$), 336, 316, 299, 274, 259, 243.

(m)
1-(N-Chloroacetylaminomethyl)-3-acetyl-5-methyl-5,6,7,8-tetrahydro-2-naphthol Starting material: 3-acetyl-5-methyl-5,6,7,8-tetrahydro-2-naphthol [described in Reference Example 2(k)].
Yield: 51%.
m.p.: 156°–157° C. (not recrystallized).
TLC (methylene chloride): Rf=0.27.
IR (KBr disc.): $\nu=3310, 2940, 2860, 1640, 1535, 1460, 1420, 1375, 1335, 1320, 1300, 1280, 1260, 1230, 1160, 1090, 1055, 1020, 975, 960, 890, 810, 790, 680, 640, 590, 550, 510, 420$ cm$^{-1}$.
NMR: $\delta=12.40$ (1H, s), 7.40 (1H, s), 7.13 (1H, broad s), 4.49 (2H, d, J=6Hz), 3.93 (2H, s), 3.10-2.60 (3H, m), 2.55 (3H, s), 2.10-1.50 (4H, m), 1.27 (3H, d, J=7Hz).

EXAMPLE 2

2-Acetyl-4-tert-butyl-6-aminomethylphenol hydrochloride

To 1.49 g of 2-acetyl-4-tert-butyl-6-(N-chloroacetylaminomethyl)phenol (prepared in Example 1) dissolved in 10 ml of ethanol were added 4.0 ml of conc. hydrochloric acid and heated at reflux for 20 hous. The reaction mixture was concentrated at reduced pressure and the residue was recrystallized from a mixed solvent of methanol and diethyl ether to give 1.19 g of the title compound having the following physical properties as white needles.
m.p.: 191°–193° C.
TLC (n-butanol:glacial acetic acid:water=5:2:3): Rf=0.73.
IR (KBr disc.): $\nu=3400, 2960, 1640, 1615, 1470, 1450, 1370, 1330, 1280, 1250, 1150, 1130, 990, 885, 820, 770, 645, 630$ cm$^{-1}$.
NMR (CD$_3$OD solution): $\delta=7.70$ (1H, d, J=2.5 Hz), 7.55 (1H, d, J=2.5 Hz), 4.75 (4H, broad s), 4.10 (2H, s), 2.60 (3H, s), 1.33 (9H, s).

In a similar manner, the compounds having the following physical properties were obtained from the corresponding N-chloroacetylaminomethyl compounds.

(a)
2-Cyclohexylcarbonyl-4-tert-butyl-6-aminomethylphenol hydrochloride

Starting material: 2-cyclohexylcarbonyl-4-tert-butyl-6-(N-chloroacetylaminomethyl)phenol [described in Example 1(a)].
Yield: 67%.
m.p.: 205–209 (white amorphous crystals).

TLC (ethyl acetate:acetic acid:water=3:1:1): Rf=0.64.

IR (KBr disc.): ν=3350, 3250, 3170, 2930, 2850, 1640, 1630, 1600, 1550, 1470, 1450, 1425, 1370, 1335, 1320, 1300, 1290, 1250, 1225, 1180, 1140, 1010, 895 cm$^{-1}$.

NMR (CD$_3$OD solution): δ=7.90 (1H, d, J=2 Hz), 7.70 (1H, d, J=2 Hz), 4.17 (2H, s), 3.30 (1H, m), 2.10–1.30 (10H, m), 1.37 (9H, s).

(b) 2-Benzoyl-4-tert-butyl-6-aminomethylphenol hydrochloride

Starting material: 2-benzoyl-4-tert-butyl-6-(N-chloroacetylaminomethyl)phenol [described in Example 1(b)].

Yield: 92%.

m.p.: 227°–228° C. (yellow amorphous crystals).

TLC (n-butanol:glacial acetic acid:water=5:2:3): Rf=0.82.

IR (KBr disc.): ν=3400, 2950, 2860, 2620, 1630, 1600, 1560, 1510, 1475, 1465, 1445, 1395, 1390, 1370, 1340, 1325, 1290, 1280, 1250, 1180, 1130, 1080, 1040, 1010, 970, 935, 900, 880, 860, 830, 815, 800, 765, 715, 695, 665, 640, 600, 540, 520, 490 cm$^{-1}$.

NMR (dimethylsulfoxide-d$_6$ solution): δ=7.80-7.27 (7H, m), 4.03 (2H, s), 1.23 (9H, s).

(c) 2-(4-Bromobenzoyl)-4-tert-butyl-6-aminomethylphenol hydrochloride

Starting material: 2-(4-bromobenzoyl)-4-tert-butyl-6-(N-chloroacetylaminomethyl)phenol [described in Example 1(c)].

Yield: 89%.

m.p.: 240°–245° C. (yellow amorphous crystals).

IR (KBr disc.): ν=3400, 3000, 2960, 1630, 1600, 1590, 1560, 1500, 1470, 1450, 1395, 1365, 1340, 1330, 1280, 1250, 1180, 1130, 1070, 1000, 900, 880, 850, 830, 810, 785, 740, 685 cm$^{-1}$.

NMR (CD$_3$OD+dimethylsulfoxide-d$_6$ solution): δ=7.83-7.33 (6H, m), 4.07 (2H, s), 1.27 (9H, s).

(d) 2-Propionyl-4-tert-butyl-6-aminomethylphenol hydrochloride

Starting material: 2-propionyl-4-tert-butyl-6-(N-chloroacetylaminomethyl)phenol [described in Example 1(d)].

Yield: 48.3%.

m.p.: 182°–184° C. (white amorphous crystals).

TLC (ethyl acetate:acetic acid:water=3:1:1): Rf=0.85.

IR (KBr disc.): ν=3400, 3200, 3080, 3040, 2960, 2920, 1630, 1610, 1570, 1500, 1450, 1380, 1360, 1290, 1270, 1230, 1090, 1055, 815, 780 cm$^{-1}$.

NMR (CD$_3$OD solution): δ=7.85 (1H, d, J=2 Hz), 7.65 (1H, d, J=2 Hz), 4.13 (2H, s), 3.15 (2H, q, J=7 Hz), 1.36 (9H, s), 1.19 (3H, t, J=7 Hz).

MS: m/e=235 (M$^+$), 220, 218, 206, 203, 189, 178, 163, 162.

(e) 2-Phenylacetyl-4-tert-butyl-6-aminomethylphenolhydrochloride

Starting material: 2-phenylacetyl-4-tert-butyl-6-(N-chloroacetylaminomethyl)phenol [described in Example 1(e)].

Yield: 70.1%.

m.p.: 196°–198° C. (pale yellow needles).

TLC (ethyl acetate:acetic acid:water=3:1:1): Rf=0.88.

IR (KBr disc.): ν=3430, 2980, 2900, 1640, 1620, 1475, 1460, 1375, 1350, 1290, 1255, 1180, 1135, 725 cm$^{-1}$.

NMR (dimethylsulfoxide-d$_6$ solution): δ=7.93 (1H, d, J=2 Hz), 7.83 (1H, d, J=2 Hz), 7.25 (5H, s), 4.48 (2H, s), 3.98 (2H, s), 1.30 (9H, s).

(f) 2-Chloroacetyl-4-tert-butyl-6-aminomethylphenol hydrochloride

Starting material: 2-chloroacetyl-4-tert-butyl-6-(N-chloroacetylaminomethyl)phenol [described in Example 1(f)].

Yield: 64.4%.

m.p.: 160° C. (dec.) (pale yellow amorphous crystals).

TLC (ethyl acetate:acetic acid:water=3:1:1): Rf=0.76.

IR (KBr disc.): ν=3425, 2970, 2900, 2870, 2850-2200, 1660, 1640, 1615, 1460, 1275, 1230 cm$^{-1}$.

NMR (CD$_3$OD solution): δ=7.82 (1H, d, J=2 Hz), 7.70 (1H, d, J=2 Hz), 4.93 (2H, s), 4.15 (2H, s), 1.35 (9H, s).

(g) 2-(4-Methylthiobenzoyl)-4-tert-butyl-6-aminomethylphenol hydrochloride

Starting material: 2-(4-methylthiobenzoyl)-4-tert-butyl-6-(N-chloroacetylaminomethyl)phenol [described in Example 1(g)].

Yield: 86.5%.

m.p.: 205°–208° C. (yellowish green amorphous crystals).

TLC (ethyl acetate:acetic acid:water=3:1:1): Rf=0.86.

IR (KBr disc.): ν=3400, 2960, 1635, 1595, 1570, 1515, 1470, 1455, 1405, 1370, 1345, 1330, 1295, 1280, 1250, 1180, 1140, 1095, 1035, 1010, 960, 900, 890, 855, 840, 815, 790 cm$^{-1}$.

NMR (CD$_3$OD solution): δ=7.90-7.15 (6H, m), 4.20 (2H, s), 2.53 (3H, s), 1.27 (9H, s).

(h) 2-Valeryl-4-tert-butyl-6-aminomethylphenol hydrochloride

Starting material: 2-valeryl-4-tert-butyl-6-(N-chloroacetylaminomethyl)phenol [described in Example 1(h)].

Yield: 68%.

m.p.: 187°–190° C. (white amorphous crystals).

TLC (butanol:acetic acid:water=5:2:3): Rf=0.75.

IR (KBr disc.): ν=3200-2500, 2950, 2850, 1650, 1620, 1450, 1410, 1380, 1360, 1340, 1290, 1270, 1230, 1130, 1100, 890, 820, 780 cm$^{-1}$.

NMR (CD$_3$OD solution): δ=7.98 (1H, d, J=2.5 Hz), 7.78 (1H, d, J=2.5 Hz), 4.20 (2H, s), 3.10 (2H, t), 2.10-1.25 (13H, m), 0.98 (3H, t).

(i) 2-Butyryl-4-tert-butyl-6-aminomethylphenol hydrochloride

Starting material: 2-butyryl-4-tert-butyl-6-(N-chloroacetylaminomethyl)phenol [described in Example 1(i)].

Yield: 56%.

m.p.: 197°–200° C. (white amorphous crystals).

TLC (butanol:acetic acid:water=5:2:3): Rf=0.81.

NMR (CD$_3$OD solution): δ=7.98 (1H, d, J=2.5 Hz) 7.80 (1H, d, J=2.5 Hz), 3.10 (2H, t), 2.01-1.60 (2H, m), 1.37 (9H, s), 1.02 (3H, t).

(j) 2-Isobutyryl-4-tert-butyl-6-aminomethylphenol hydrochloride

Starting material: 2-isobutyryl-4-tert-butyl-6-(N-chloroacetylaminomethyl)phenol [described in Example 1(j)].

Yield: 26%.

m.p.: 180°–192° C. (white needles)

TLC (butanol:acetic acid:water = 5:2:3): Rf = 0.85.

IR (KBr disc.): $\nu$ = 3450, 2950, 2850, 3300-2500, 1640, 1610, 1470, 1370, 1280, 1240, 1130, 1100, 1060, 1040, 940, 900, 840, 820, 800 cm$^{-1}$.

NMR (CD$_3$OD solution): $\delta$ = 8.00 (1H, d, J = 2.5 Hz), 7.79 (1H, d, J = 2.5 Hz), 4.20 (2H, s), 3.78 (1H, m), 1.36 (9H, s), 1.23 (6H, d).

(k) 2-(3-Methylthiopropionyl)-4-tert-butyl-6-aminomethylphenol hydrochloride

Starting material: 2-(3-methylthiopropionyl)-4-tert-butyl-6-(N-chloroacetylaminomethyl)phenol [described in Example 1(k)].

Yield: 38.1%.

m.p.: 162°–163° C. (pale yellow amorphous crystals).

TLC (the organic phase of diethyl ether:acetic acid:water = 3:1:1 was used): Rf = 0.72.

IR (KBr disc.): $\nu$ = 3425, 3060, 3030, 2980, 2940, 1640, 1620, 1475, 1450, 1375, 1280, 1125, 1105 cm$^{-1}$.

NMR (CD$_3$OD + CCl$_4$ solution): $\delta$ = 7.67 (2H, s), 4.08 (2H, s), 3.56-2.66 (4H, m), 2.10 (3H, s), 1.30 (9H, s).

MS: m/e = 281 (M$^+$), 264, 246, 233, 190, 175, 162.

(l) 2-Trifluoroacetyl-4-tert-butyl-6-aminomethylphenol hydrochloride

Starting material: 2-trifluoroacetyl-4-tert-butyl-6-(N-chloroacetylaminomethyl)phenol [described in Example 1(l)].

Yield: 83%.

m.p.: 180°–186° C. (yellow amorphous crystals)

TLC (ethyl acetate:acetic acid:water = 3:1:1): Rf = 0.70.

IR (KBr disc.): $\nu$ = 2950, 2860, 1670, 1610, 1460, 1395, 1385, 1370, 1330, 1280, 1210, 1150, 1040, 1020, 790, 720, 690 cm$^{-1}$.

NMR (CD$_3$OD solution) $\delta$ = 7.56-7.38 (2H, m), 4.16 (2H, s), 1.31 (9H, s).

(m) 1-Aminomethyl-3-acetyl-5-methyl-5,6,7,8-tetrahydro-2-naphthol hydrochloride

Starting material: 1-(N-chloroacetylaminomethyl)-3-acetyl-5-methyl-5,6,7,8-tetrahydro-2-naphthol [described in Example 1(m)].

Yield: 90%.

m.p.: ≧230° C. (dec.) (pale yellow amorphous crystals).

TLC (butanol:acetic acid:water = 5:2:3): Rf = 0.75.

IR (KBr disc.): $\nu$ = 3400, 2900, 1635, 1485, 1460, 1420, 1370, 1310, 1280, 1230, 1165, 1110, 880, 780 cm$^{-1}$.

NMR (CDCl$_3$ + CD$_3$OD solution): $\delta$ = 7.63 (1H, s), 4.67 (4H, s), 4.13 (2H, s), 2.85 (3H, m), 2.60 (3H, s), 2.30-1.50 (4H, m), 1.30 (4H, d, J = 7 Hz).

MS: m/e = 233 (M$^+$), 216, 201, 173.

EXAMPLE 3

2-Nicotinyl-4-tert-butyl-6-aminomethylphenol (a) 2-[1'-Hydroxy-1'-(3-pyridyl)methyl]-4-tert-butylanisole 270 mg of magnesium was suspended in 2 ml of anhydrous diethyl ether and 0.5 ml of a solution of 2-iodo-4-tert-butylanisole (prepared by dissolving 2.90 g of the anisole in 5 ml of diethyl ether), followed by warming the mixture to initiate the reaction. Upon addition of the remaining ethereal solution of the anisole, the mixture began to reflux. The mixture was refluxed for 30 minutes and then cooled to 0° C., and 1.03 ml of nicotinaldehyde dissolved in 5 ml of diethyl ether was added dropwise to the mixture. After stirring for one hour at 0° C., a saturated aqueous solution of ammonium chloride was added to the mixture which was then extracted with ethyl acetate. The ethyl acetate layer was washed successively with water and an aqueous sodium chloride solution, dried and concentrated. The residue was chromatographed on silica gel column using a mixed solvent of methylene chloride and ethyl acetate (1:1 by volume) as an eluting agent to give 1.76 g of the title compound having the following physical properties.

TLC (methylene chloride:ethyl acetate = 1:2): Rf = 0.20.

IR (KBr disc.): $\nu$ = 3180, 2950, 1610, 1595, 1500, 1460, 1430, 1365, 1280, 1250, 1185, 1135, 1110, 1055, 1030, 845, 805 cm$^{-1}$.

NMR (CDCl$_3$ solution): $\delta$ = 8.03-8.43 (2H, m), 6.83-7.70 (4H, m), 6.60 (1H, d, J = 8 Hz), 5.90 (1H, s), 3.85-4.60 (1H, broad), 3.63 (3H, s), 1.27 (9H, s).

(b) 2-Nicotinyl-4-tert-butylanisole 1.67 g of the compound as prepared in Example 1 (a) above was dissolved in 200 ml of methylene chloride and 15 g of magnesium dioxide was added thereto followed by stirring for 1.5 hours. The mixture was filtered and the filtrate was concentrated to obtain 1.61 g of the title compound having the following physical properties.

TLC (methylene chloride:ethyl acetate = 1:2): Rf = 0.60.

IR: $\nu$ = 2960, 1660, 1610, 1590, 1500, 1460, 1420, 1405, 1370, 1335, 1310, 1260, 1180, 1135, 1105, 1025, 970, 855, 820 cm$^{-1}$.

NMR (CDCl$_3$ solution): $\delta$ = 8.77 (1H, d, J = 2 Hz), 8.50-8.72 (1H, dd, J = 2 Hz, 5 Hz), 7.87-8.17 (1H, m), 7.10-7.60 (3H, m), 6.70-7.00 (1H, d, J = 8 Hz), 3.62 (3H, s), 1.30 (9H, s).

MS: m/e = 269 (M$^+$).

(c) 2-Nicotinyl-4-tert-butylphenol 1.56 g of the compound obtained in Example 3 (b) above was dissolved in 6 ml of acetic acid and 1.2 ml of 57% hydroiodic acid and 1.0 ml of 47% hydrobromic acid were added thereto, followed by heat-refluxing for 30 hours. The mixture was concentrated under reduced pressure, water was added to the residue and the mixture was extracted with ethyl acetate. The ethyl acetate extract was washed with water, dried, concentrated, and the residue was chromatographed on silica gel column using a mixed solvent of methylene chloride: ethyl acetate (20:1 by volume) as an eluting agent to obtain 510 mg of the title compound having the following properties.

TLC (methylene chloride: ethyl acetate=1:2): Rf=0.65.

NMR (CDCl₃ solution): δ=11.50 (1H, s), 8.53=8.85 (2H, m), 7.70—8.00 (1H, m), 7.05—7.60 (3H, m), 6.83 (1H, d, J=8 Hz), 1.23 (9H, s).

MS: m/e=255 (M+).

(d) 2-Nicotinyl-4-tert-butyl-6-(N-α-chloroacetoaminomethyl)phenol 450 mg of the compound obtained in Example 3 (c) above was dissolved in 2 ml of a mixed solvent of acetic acid: sulfuric acid (1:1 by volume), and 330 mg of N-hydroxymethyl α-chloroacetamide was added to the solution. The mixture was then stirred at 60° C. for 2 hours and at 80° C. for 1 hour and poured into water. The mixture was extracted with ethyl acetate, and the ethyl acetate layer was washed successively with water and an aqueous sodium chloride solution, dried and concentrated. The residue was chromatographed on silica gel column using a mixed solvent of methylene chloride: ethyl acetate (5:1 by volume) to obtain 390 mg of the title compound having the following physical properties.

TLC (methylene chloride: ethyl acetate=1:2): Rf=0.30.

IR (chloroform solution): ν=3430, 2960, 1670, 1630, 1590, 1530, 1460, 1415, 1370, 1345, 1275, 1250, 1130, 1100, 1055, 1020, 995 cm⁻¹.

NMR (CDCl₃ solution): δ=12.10 (1H, s), 8.47–8.85 (2H, m), 7.70–8.00 (1H, m), 7.10–7.60 (4H, m), 4.48 (2H, d, J=6 Hz), 3.98 (2H, s), 1.23 (9H, s).

MS: m/e=360 (M+).

(e) 2-Nicotinyl-4-tert-butyl-6-aminomethylphenol hydrochloride 370 mg of the compound obtained in Example 3 (d) was dissolved in 2 ml of ethanol and 1.5 ml of concentrated hydrochloric acid was added thereto followed by heat-refluxing for 24 hours. The residue was dissolved in a small amount of methanol and diethyl ether was added to the solution. The precipitated crystals were filtered to obtain 290 mg of the title compound as yellow crystals having the following physical properties.

m.p.: 158°–163° C.

IR (KBr disc.): ν=3400, 2960, 1630, 1460, 1370, 1350, 1260, 1195, 1120, 1015, 900, 830 cm⁻¹.

NMR (CD₃OD solution): δ=9.20–9.30 (1H, m), 9.05–9.20 (1H, m), 8.80–9.05 (1H, m), 8.20–8.45 (1H, m), 7.95 (1H, d, J=2 Hz), 7.61 (1H, d, J=2 Hz), 4.29 (2H, s), 1.32 (9H, s).

EXAMPLE 4

1-Propionyl-3-aminomethyl-5,6,7,8-tetrahydro-2-naphthol hydrochloride (a) 1-Propionyl-3-acetylaminomethyl-5,6,7,8-tetrahydro-2-naphthol 1.45 g of 3-propionyl-3-acetylaminomethyl-5,6,7,8-tetrahydro-2-naphthylpropionate was dissolved in 5 ml of methylene chloride and 2.0 g of aluminum chloride was added to the solution. After a homogeneous solution was formed, methylene chloride was distilled off from the reaction system while raising temperature and solution was heated at 100° C. for 10 minutes. After allowing the solution to cool, water was added thereto, and the mixture was extracted with ethyl acetate. The ethyl acetate layer was washed successively with water, an aqueous solution bicarbonate solution and an aqueous sodium chloride solution, dried and concentrated. The residue was chromatographed on silica gel column using a mixed solvent of methylene chloride: ethyl acetate (10:1 by volume) to obtain 640 mg of the title compound having the following physical properties.

m.p.: 136°-140° C.

TLC (methylene chloride: ethyl acetate=4:1): Rf=0.57.

IR (KBr disc): ν=3300, 3100, 2980, 2930, 2890, 2860, 1700, 1610, 1560, 1470, 1410, 1380, 1365, 1295, 1270, 1245, 1120, 1075, 1050, 1020, 950 cm⁻¹.

NMR (CDCl₃ solution): δ=9.93 (1H, s), 6.79 (1H, s), 6.70-7.05 (1H, broad), 4.20 (2H, d, J=6.5 Hz), 2.84 (2H, q, J=7.5 Hz), 2.40–2.80 (4H, m), 2.20 (2H, q, J=7.5 Hz), 1.50–1.90 (4H, m), 1.14 (3H, t, J=7.5 Hz), 1.08 (3H, t, J=7.5 Hz).

MS: m/e=289 (M+).

(b) 1-Propionyl-3-aminomethyl-5,6,7,8-tetrahydro-2-naphthol hydrochloride

To 400 mg of the compound obtained in Example 4 (a) above were added 2 ml of methanol and 1 ml of concentrated hydrochloric acid followed by refluxing for 15 hours. The mixture was concentrated, and the residue was washed with diethyl ether and dissolved in methanol. Activated carbon was added to the solution which was then filtered. Diethyl ether was added to the filtrate and the precipitated crystals were filtered to obtain 160 mg of the title compound having the following physical properties.

IR (KBr disc.): ν=3100, 2940, 1695, 1580, 1500, 1470, 1435, 1380, 1355, 1250, 1120, 1080, 945 cm⁻¹.

NMR (CD₃OD-CDCl₃ solution): δ=7.14 (1H, s), 4.10 (2H, s), 2.89 (2H, q, J=7.5 Hz), 2.40–3.00 (4H, m), 1.50–2.00 (4H, m), 1.18 (3H, t, J=7.5 Hz).

MS: m/e=233 (M+).

EXAMPLE 5

1-Acetyl-3-aminomethyl-5,6,7,8-tetrahydro-2-naphthol hydrochloride (a) 1-Acetyl-3-acetylaminomethyl-5,6,7,8-tetrahydro-2-naphthol 1.30 g of 3-acetylaminomethyl-5,6,7,8-tetrahydro-2-naphthyl acetate was dissolved in 5 ml of methylene chloride and 2.0 g of aluminum chloride was added to the solution. The resulting mixture was then worked up in the same manner as described in Example 3 to obtain 260 mg of the title compound having the following physical properties.

TLC (methylene chloride: ethyl acetate=1:1): Rf=0.50.

IR (KBr disc): ν=3250, 3100, 2920, 1700, 1610, 1440, 1380, 1360, 1310, 1270, 1245, 1155, 1105, 1020, 710 cm⁻¹.

NMR (CDCl₃ solution): δ=10.17 (1H,s), 6.77 (1H, s), 6.50-7.10 (1H, broad), 4.17 (2H, d, J=6 Hz), 2.40-3.00 (4H, m), 2.50 (3H, s), 1.93 (3H, s), 1.50-2.10 (4H, m).

(b) 1-Acetyl-3-aminomethyl-5,6,7,8-tetrahydro-2-naphthol hydrochloride 195 mg of the compound obtained in (a) above was dissolved in 3 ml of ethanol and 0.5 ml of concentrated hydrochloric acid was added thereto followed by refluxing for 16 hours. The reaction mixture was concentrated under reduced pressure and the residue was washed with diethyl ether and dissolved in a small amount of methanol. The solution was filtered, and diethyl ether was added to the filtrate. The precipitated crystals were filtered and recrystallized from methanol-diethyl ether to obtain 130 mg of the title compound.

NMR (CD$_3$OD-CCl$_4$ solution): δ=7.16 (1H, s), 4.07 (2H, s), 2.50–3.00 (4H, m), 2.56 (3H, s), 1.50–2.00 (4H, m).

EXAMPLE 6

2-Propionyl-4-methylthio-6-aminomethylphenol hydrochloride

(a) 4-Methylthio-2-propionylphenol 5.8 g of titanium chloride was added to 6.0 g of 4-methylthiophenylpropionate and the mixture was heated at 150° C. for 10 minutes. After allowing the mixture to cool, chloroform and ice water were added thereto followed by addition of concentrated hydrochloric acid. The aqueous layer was separated and extracted with chloroform. The combined chloroform layer was washed with water, dried and concentrated. The residue was chromatographed on silica gel column using a mixed solvent of ethyl acetate: benzene (1:40 by volume) as an eluting agent to obtain 2.16 g of the title compound.

TLC (ethyl acetate: benzene=1:10): Rf=0.80.

IR (KBr disc.): ν=3400, 3000, 2950, 1640, 1610, 1475, 1440, 1415, 1370, 1355, 1280, 1245, 1190, 1015, 970, 810, 800 cm$^{-1}$.

NMR (CDCl$_3$ solution): δ=12.25 (1H, s), 7.74 (1H, d, J=2 Hz), 7.45 (1H, dd, J=2 Hz, 9 Hz), 6.92 (1H, d, J=9 Hz), 3.02 (2H, q, J=7 Hz), 2.45 (3H, s), 1.22 (3H, t, J=7 Hz).

MS: m/e 196 (M+), 167, 139, 78.

(b) 2-Propionyl-4-methylthio-6-(N-α-chloroacetylaminomethyl)phenol 2.16 g of the compound obtained in (a) above was dissolved in a mixture of 15 ml of acetic acid and 15 ml of sulfuric acid, and 2.0 g of N-hydroxymethyl chloroacetamide was added to the solution followed by stirring at 50° C. for 2 hours. The reaction mixture was poured into ice water and extracted with ethyl acetate. The extract was washed successively with water and an aqueous sodium chloride solution, dried and then concentrated. The resulting residue was chromatographed on silica gel column using a mixed solvent of ethyl acetate: benzene (1:3 by volume) as an eluting agent to obtain 1.62 g of the title compound having the following physical properties.

TLC (ethyl acetate: benzene=1:10): Rf=0.30.

NMR (CDCl$_3$ solution): δ=7.63 (1H, d, J=2.5 Hz), 7.42 (1H, d, J=2.5 Hz), 4.45 (2H, d, J=6 Hz), 4.00 (2H, s), 3.02 (2H, q, J=7 Hz), 2.43 (3H, s), 1.23 (3H, t, J=7 Hz).

MS: m/e 301 (M+), 224, 208, 179.

678 mg of the compound obtained in (b) above was dissolved in 10 ml of ethanol and 2 ml of concentrated hydrochloric acid was added to the solution followed by heat-refluxing for 20 hours. The reaction mixture was concentrated under reduced pressure and the residue was recrystallized from ethanol to obtain 287 mg of the title compound having the following physical properties.

m.p.: 202°–204° C.

TLC (n-butanol: acetic acid: water=10:1:1): Rf=0.58.

IR (KBr disc.): ν=3400, 2970, 2910, 1640, 1610, 1450, 1380, 1275, 1110, 820, 770 cm$^{-1}$.

NMR (CD$_3$OD solution): δ=7.92 (1H, d, J=2.4 Hz), 7.68 (1H, d, J=2.4 Hz), 4.78 (3H, broad), 4.18 (2H, s), 3.15 (2H, q, J=7.4 Hz), 2.51 (3H, s), 1.21 (3H, t, J=7.4 Hz).

MS: m/e 225 (M+), 208, 179, 161.

While the invention has been described in detail and with reference to specific embodiments thereof, it will be apparent to one skilled in the art that various changes and modifications can be made therein without departing from the spirit and scope thereof.

What is claimed is:

1. A 2-acyl-6aminomethylphenol compound having the formula (I):

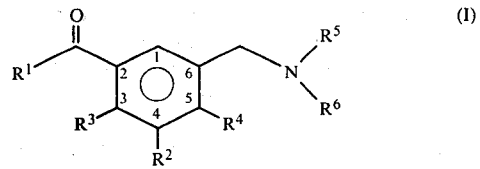

wherein R$^1$ represents a straight chain or branched chain alkyl group of 1 to 6 carbon atoms unsubstituted or substituted with 1 to 3 halogen atoms; a hydrogen atom or a group having the formula (II):

wherein n represents 0 or an integer of 1 to 6; R$^7$ represents a cycloalkyl group of 3 to 8 carbon atoms unsubstituted or substituted with at least one lower alkyl group; a phenyl group unsubstituted or substituted with at least one lower alkyl group, a halogen atom, a lower alkoxy group or a lower alkylthio group; a lower alkoxy group; a lower alkylthio group; a lower alkylsulfinyl group; a lower alkylsulfonyl group; an N-lower alkylamino group; an N,N-di-lower alkylamino group; or a pyridyl, furyl or thienyl group; R$^2$ represents a straight chain or branched chain alkyl group of 1 to 6 carbon atoms; a cycloalkyl group of 4 to 8 carbon atoms unsubstituted or substituted with at least one lower alkyl group; or a phenyl group unsubstituted or substituted with at least one lower alkyl group, a lower alkoxy group, a lower alkylthio group or a halogen atom; or a lower alklythio group; R$^3$ and R$^4$ each represents a hydrogen atom or R$^2$ and R$^3$ or R$^2$ and R$^4$ when taken together represent an alkylene group of 2 to 5 carbon atoms unsubstituted or substituted with 1 or 2 lower alkyl groups; R$^5$ represents a hydrogen atom or a lower alkyl group; and R$^6$ represents a hydrogen atom, a lower alkyl group a formyl group, an alkanoyl group of 2 to 5 carbon atoms unsubstituted or substituted with a halogen or a benzoyl group unsubstituted or substituted with at least one lower alkyl group, a hydroxy group or a halogen atom, and the pharmaceutically acceptable acid addition salt thereof.

2. 2-Acetyl-4-tert-butyl-6-aminomethylphenol according to claim 1.

3. 2-Propionyl-4-tert-butyl-6-aminomethylphenol according to claim 1.

4. 2-Butyryl-4-tert-butyl-6-aminomethylphenol according to claim 1.
5. 2-Isobutyryl-4-tert-butyl-6-aminomethylphenol according to claim 1.
6. 2-Valeryl-4-tert-butyl-6-aminomethylphenol according to claim 1.
7. 2-Chloroacetyl-4-tert-butyl-6-aminomethylphenol according to claim 1.
8. 2-Trifluoroacetyl-4-tert-butyl-6-aminomethylphenol according to claim 1.
9. 2-Cyclohexylcarbonyl-4-tert-butyl-6-aminomethylphenol according to claim 1.
10. 2-Benzoyl-4-tert-butyl-6-aminomethylphenol according to claim 1.
11. 2-(4-Bromobenzoyl)-4-tert-butyl-6-aminomethylphenol according to claim 1.
12. 2-(4-Methylthiobenzoyl)-4-tert-butyl-6-aminomethylphenol according to claim 1.
13. 2-Phenylacetyl-4-tert-butyl-6-aminomethylphenol according to claim 1.
14. 2-(3-Methylthiopropionyl)-4-tert-butyl-6-aminomethylphenol according to claim 1.
15. 1-Aminomethyl-3-acetyl-5-methyl-5,6,7,8-tetrahydro-2-naphthol according to claim 1.
16. 1-Acetyl-3-aminomethyl-5,6,7,8-tetrahydro-2-naphthol according to claim 1.
17. 1-Propionyl-3-aminomethyl-5,6,7,8-tetrahydro-2-naphthol according to claim 1.
18. 2-Nicotinyl-4-tert-butyl-6-aminomethylphenol according to claim 1.
19. 2-Propionyl-4-methylthio-6-aminomethylphenol according to claim 1.
20. 2-Acetyl-4-tert-butyl6-(N-chloroacetylaminomethyl)phenol according to claim 1.
21. 2-Propionyl-4-tert-butyl-6-(N-chloroacetylaminomethyl)phenol according to claim 1.
22. 2-Butyryl-4-tert-butyl-6-(N-chloroacetylaminomethyl)phenol according to claim 1.
23. 2-Isobutyryl-4-tert-butyl-6-(N-chloroacetylaminomethyl)phenol according to claim 1.
24. 2-Valeryl-4-tert-butyl-6-(N-chloroacetylaminomethyl)phenol according to claim 1.
25. 2-Chloroacetyl-4-tert-butyl-6-(N-chloroacetylaminomethyl)phenol according to claim 1.
26. 2-Trifluoroacetyl-4-tert-butyl-6-(N-chloroacetylaminomethyl)phenol according to claim 1.
27. 2-Cyclohexylcarbonyl-4-tert-butyl-6-(N-chloroacetylaminomethyl)phenol according to claim 1.
28. 2-Benzoyl-4-tert-butyl-6-(N-chloroacetylaminomethyl)phenol according to claim 1.
29. 2-(4-Bromobenzoyl)-4-tert-butyl-6-(N-chloroacetylaminomethyl)phenol according to claim 1.
30. 2-(4-Methylthiobenzoyl)-4-tert-butyl-6-(N-chloroacetylaminomethyl)phenol according to claim 1.
31. 2-Phenylacetyl-4-tert-butyl-6-(N-chloroacetylaminomethyl)phenol according to claim 1.
32. 2-(3-Methylthiopropionyl)-4-tert-butyl-6-(N-chloroacetylaminomethyl)phenol according to claim 1.
33. 1-(N-Chloroacetylaminomethyl)-3-acetyl-5-methyl-5,6,7,8-tetrahydro-2-naphthol according to claim 1.
34. 1-Acetyl-3-(N-acetylaminomethyl)-5,6,7,8-tetrahydro-2-naphthol according to claim 1.
35. 1-Propionyl-3-(N-propionylaminomethyl)-5,6,7,8-tetrahydro-2-naphthol according to claim 1.
36. 2-Nicotinyl-4-tert-butyl-6-(N-chloroacetylaminomethyl)phenol according to claim 1.
37. 2-Propionyl-4-methylthio-6-(N-chloroacetylaminomethyl)phenol according to claim 1.

* * * * *